US009439852B2

(12) United States Patent
Bleier

(10) Patent No.: US 9,439,852 B2
(45) Date of Patent: *Sep. 13, 2016

(54) METHODS OF DELIVERING PHARMACEUTICAL AGENTS

(71) Applicant: Massachusetts Eye & Ear Infirmary, Boston, MA (US)

(72) Inventor: Benjamin S. Bleier, Weston, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 100 days.

This patent is subject to a terminal disclaimer.

(21) Appl. No.: 14/739,872

(22) Filed: Jun. 15, 2015

(65) Prior Publication Data
US 2015/0283071 A1 Oct. 8, 2015

Related U.S. Application Data

(63) Continuation of application No. 14/589,025, filed on Jan. 5, 2015, now Pat. No. 9,084,756, which is a continuation of application No. 14/172,349, filed on Feb. 4, 2014, now Pat. No. 8,945,600, which is a continuation of application No. 13/561,998, filed on Jul. 30, 2012, now Pat. No. 8,673,338.

(60) Provisional application No. 61/513,069, filed on Jul. 29, 2011.

(51) Int. Cl.

| | |
|---|---|
| *A61F 13/00* | (2006.01) |
| *A61F 2/00* | (2006.01) |
| *A61K 9/14* | (2006.01) |
| *A61K 38/00* | (2006.01) |
| *A61N 1/30* | (2006.01) |
| *A61M 31/00* | (2006.01) |
| *A61M 37/00* | (2006.01) |
| *A61F 2/02* | (2006.01) |
| *A61F 2/28* | (2006.01) |
| *A61K 9/00* | (2006.01) |
| *A61K 31/137* | (2006.01) |
| *A61K 31/485* | (2006.01) |
| *A61K 31/473* | (2006.01) |
| *A61K 38/18* | (2006.01) |
| *A61K 47/36* | (2006.01) |
| *A61K 47/38* | (2006.01) |

(52) U.S. Cl.
CPC ........... *A61K 9/0085* (2013.01); *A61K 31/137* (2013.01); *A61K 31/473* (2013.01); *A61K 31/485* (2013.01); *A61K 38/18* (2013.01); *A61K 38/185* (2013.01); *A61K 47/36* (2013.01); *A61K 47/38* (2013.01); *A61M 31/00* (2013.01)

(58) Field of Classification Search
None
See application file for complete search history.

(56) References Cited

PUBLICATIONS

Bernal-Sprekelsen et al., "Closure of cerebrospinal fluid leaks prevents ascending bacterial meningitis," Rhinology, 43:277-281 (2005).
Bleier et al., "Antibiotic eluting chitosan glycerophosphate implant in the setting of acute bacterial sinusitis: a rabbit model," Am. J. Rhinol. Allergy, 24:129-132 (2010).
Bleier et al., "Chitosan glycerophasphate-based semirigid dexamethasone eluting biodegradable stent," Am. J. Rhinol. Allergy., 23(1):76-79 (2009) (Abstract Only).
Bleier et al., "Current management of juvenile nasopharyngeal angiofibroma: A tertiary center experience 1999-2007," Am. J. Rhinol. Allergy, 23:328-330 (2009).
Bleier et al., "Laser-assisted cerebrospinal fluid leak repair: an animal model to test feasibility," Otolaryngol. Head Neck Surg., 137:810-814 (2007).
Bleier et al., "Mucocele Rate Following Endoscopic Skull Base Reconstruction Using Vascularized Pedicled Flaps," Am. J. Rhinol. Allergy, 25:186-187 (2011).
Bleier et al., "Temporospatial quantification of fluorescein-labeled sinonasal irrigation delivery," Int. Forum Allergy Rhinol., 1:361-365 (2011).
Bleier et al., PLOS One, 8(4):1-7 (2013).
Brookmeyer et al., "Forecasting the global burden of Alzheimer's disease," Alzheimer's & Dementia, 3:186-191 (2007).
Cardoso et al., "Looking at the blood-brain barrier: Molecular anatomy and possible investigation approaches," Brain Research Reviews, 64:328-363 (2010).
Chiu et al., "An anatomical study of the arteries of the anterior nasal septum," Otolaryngol. Head Neck Surg., 134(1):33-36 (2006) (Abstract Only).
Dhuria et al., "Intranasal delivery to the central nervous system: mechanisms and experimental considerations," J. Pharm. Sci., 99:1654-1673 (2010).
Luppi et al., "Chitosan-based Hydrogels for Nasal Drug Delivery: from Inserts to Nanoparticles," Expert Opin. Drug Deliv., 7(7):811-828 (2010).

(Continued)

*Primary Examiner* — Jeffrey T Palenik
(74) *Attorney, Agent, or Firm* — Fish & Richardson P.C.

(57) ABSTRACT

Provided are methods of delivering at least one pharmaceutical agent to the central nervous system (CNS) of a subject, methods of treating a neurological disorder or pain in a subject that include administering at least one pharmaceutical agent onto a SEM graft in the skull base of the subject. Also provided are methods of treating a neurological disorder or pain in a subject that include forming a SEM graft in the skull base of the subject and administering at least one pharmaceutical agent onto the SEM graft in the skull base of the subject. Also provided are methods of forming a SEM graft in the skull base of a subject, compositions for administration onto a SEM graft in the skull base or into an endonasal reservoir or endonasal reservoir device in a subject, and devices for administering such compositions onto a SEM graft in the skull base of a subject.

23 Claims, 11 Drawing Sheets
(4 of 11 Drawing Sheet(s) Filed in Color)

(56) References Cited

PUBLICATIONS

Merkus et al., "Can nasal drug delivery bypass the blood-brain barrier?: Questioning the direct transport theory," Drugs R. D., 8:133-144 (2007).

Modi et al., "Advances in the treatment of neurodegenerative disorders employing nanotechnology," Ann. NY Acad. Sci., 1184:154-172 (2010).

Nance et al., "A dense poly(ethylene glycol) coating improves penetration of large polymeric nanoparticles within brain tissue," Sci. Transl. Med., 4:149ra119 (2012).

Ngwuluka et al., "Levodopa delivery systems: advancements in delivery of the gold standard," Expert Opin. Drug Deliv., 7:203-224 (2010).

Ranganath et al., "Hydrogel Matrix Entrapping PLGA-Paclitaxel Microspheres: Drug Delivery with Near Zero-Order Release and Implantability Advantages for Malignant Brain Tumour Chemotherapy," Pharm. Res., 26(9):2101-2114 (2009).

Soichet et al., "Cell delivery to the central nervous system," Adv. Drug Deliv. Rev., 42:81-102 (2000).

Zhao et al., "Intranasal delivery of nerve growth factor to protect the central nervous system against acute cerebral infarction," Chin. Med. Sci. J., 19:257-261 (2004).

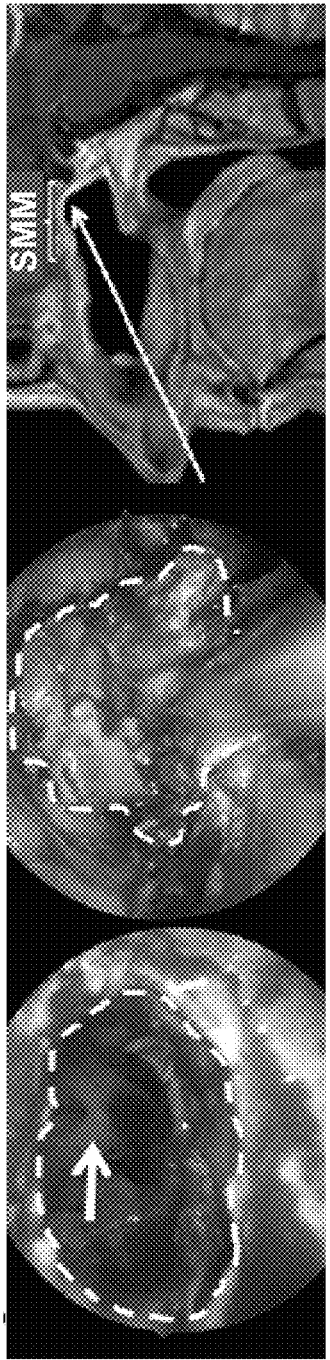
FIG. 10C
FIG. 10B
FIG. 10A
SMM = SEM graft in the skull base
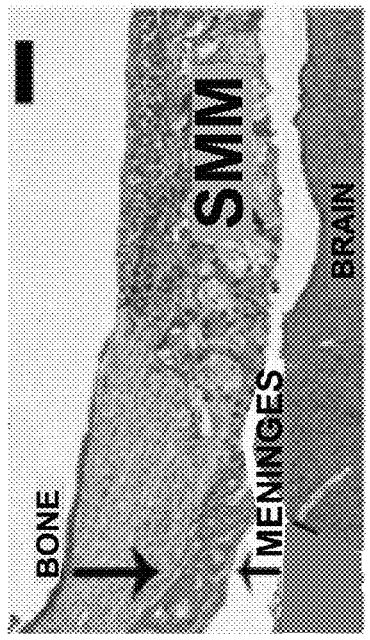
FIG. 11
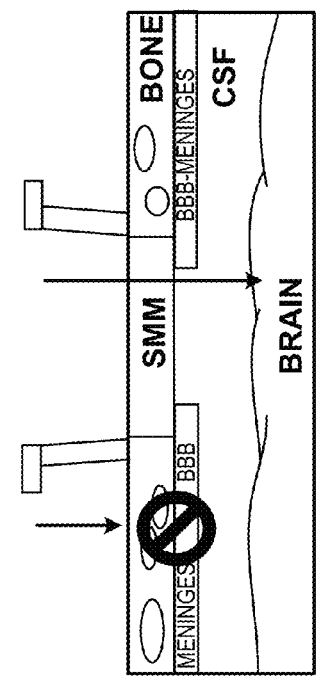
FIG. 12

US 9,439,852 B2

METHODS OF DELIVERING PHARMACEUTICAL AGENTS

CLAIM OF PRIORITY

The present application is a continuation of U.S. patent application Ser. No. 14/589,025, filed on Jan. 5, 2015, now U.S. Pat. No. 9,084,756, which is a continuation of U.S. patent application Ser. No. 14/172,349, filed on Feb. 4, 2014, now U.S. Pat. No. 8,945,600, which is a continuation of U.S. patent application Ser. No. 13/561,998, filed Jul. 30, 2012, now U.S. Pat. No. 8,673,338, which claims the benefit of U.S. Provisional Patent Application No. 61/513,069, filed on Jul. 29, 2011. The entire contents of the foregoing are hereby incorporated by reference herein.

TECHNICAL FIELD

This invention relates to methods of delivering pharmaceutical agents to the central nervous system of a subject, e.g., for treating neurological disorders and pain.

BACKGROUND

Neurological disorders affect more than 20 million patients in the U.S. alone and account for over $400 billion in annual expenditure for both their treatment and chronic care (Shoichet et al., *Adv. Drug Deliv. Rev.* 42:81-102, 2000). As the population continues to age, the incidence and health care costs associated with neurological disorders are projected to rise considerably. In 2006, the world-wide prevalence of Alzheimer's disease alone was 26.6 million, and this number is expected to quadruple by 2050 (Brookmeyer et al., *Alzheimers Dement.* 3:186-191, 2007). The scale of this disease burden suggests that therapies capable of delaying or treating neurological disorders will translate into enormous cost savings to the global health care system.

The paucity of effective neurological disorder therapies is at least partially attributable to the presence of the blood-brain-barrier (BBB). The BBB excludes or prevents many potential therapeutic agents from reaching the central nervous system (CNS). The BBB performs this function by excluding molecules having specific physical and/or electrochemical properties, by metabolizing molecules, and by effluxing molecules. The BBB has been estimated to prevent up to 98% of all potential neuropharmaceutical agents from reaching the CNS (Cardoso et al., *Brain Res. Rev.* 64:328-363, 2010). Due to the activity of the BBB, known polar, charged, and macromolecular agents that may be capable of treating neurological disorders are clinically ineffective due to their inability to cross the BBB to reach the CNS.

SUMMARY

This invention is based, in part, on the discovery that a semipermeable epithelial membrane (SEM) graft can be successfully placed in the skull base of a patient. The placement of the SEM graft in this location allows therapeutic agent(s), placed onto the SEM graft (on the sinus or nasal cavity side), to enter the CNS of the subject.

Thus, provided herein are methods of delivering a (e.g., at least one) pharmaceutical agent to the CNS of a subject. These methods include directly administering the pharmaceutical agent onto a SEM graft in the skull base of the subject. In some embodiments, the pharmaceutical agent is administered into an endonasal reservoir or an endonasal reservoir device in the subject. In some embodiments, the pharmaceutical agent is delivered to the brain of the subject.

Also provided are methods of treating a neurological disorder in a subject having a SEM graft in their skull base. These methods include directly administering a (e.g., at least one) pharmaceutical agent onto the SEM graft in the skull base of the subject. In some embodiments, the pharmaceutical agent is administered into an endonasal reservoir. In some embodiments of any of the methods described herein, the pharmaceutical agent is placed into an endonasal reservoir device in an endogenous sinus tissue of the subject (e.g., an endonasal reservoir device previously implanted into the endogenous sinus tissue of the subject), where the device contains an (e.g., at least one) opening or permeable surface proximal to the SEM graft in the skull base and the pharmaceutical agent placed in the endonasal reservoir device is administered onto the SEM graft in the skull base.

Additional methods of treating a neurological disorder in a subject are provided. These methods include forming a SEM graft in the skull base of the subject and administering a (e.g., at least one) pharmaceutical agent onto the SEM graft in the skull base of the subject. Some embodiments of these methods further include introducing a SEM graft over an endogenous sinus tissue or at a position proximal to the SEM graft in the skull base, where the SEM graft in the endogenous sinus tissue forms an endonasal reservoir. Some embodiments, further include introducing or implanting an endonasal reservoir device containing an (e.g., at least one) opening or permeable surface into an endogenous sinus tissue of the subject and placing the pharmaceutical agent into the endonasal reservoir device, where the opening or permeable surface is proximal to the SEM graft in the skull base and the pharmaceutical agent in the endonasal reservoir device is administered onto the SEM graft in the skull base.

Also provided are methods of treating pain (e.g., chronic pain) in a subject having a SEM graft in their skull base. These methods include directly administering an (e.g., at least one) analgesic onto the SEM graft in the skull base of the subject. In some embodiments, the analgesic is administered into an endonasal reservoir. In some embodiments, the analgesic is placed into an endonasal reservoir device in an endogenous sinus tissue of the subject, where the device contains an (e.g., at least one) opening or permeable surface proximal to the SEM graft in the skull base and the analgesic placed in the endonasal reservoir device is administered onto the SEM graft in the skull base.

Additional methods of treating pain in a subject are provided. These methods include forming a SEM graft in the skull base of the subject; and administering a (e.g., at least one) analgesic onto the SEM graft in the skull base of the subject. In some embodiments, the methods further include introducing a SEM graft over an endogenous sinus tissue or in a position proximal to the SEM graft in the skull base, where the SEM graft in the endogenous sinus tissue forms an endonasal reservoir. In some embodiments, the methods further include introducing an endonasal reservoir device containing an (e.g., at least one) opening or permeable surface into an endogenous sinus tissue of the subject and placing the analgesic into the endonasal reservoir device, where the opening or permeable surface is proximal to the SEM graft in the skull base and the analgesic in the endonasal reservoir device is administered onto the SEM graft in the skull base.

In any of the methods described herein, the forming, introducing, placing or administering is performed by an endoscopic procedure (e.g., an endoscopic procedure through the subject's nasal canal). In any of the methods described herein, the forming, introducing, placing, or administering is performed by an interfacial procedure (e.g., injection or insertion through the subject's facial tissue), or an intracranial procedure (e.g., injection or insertion through the subjects cranium).

In some embodiments of any of the methods described herein, the SEM graft in the skull base and/or the SEM graft in the endogenous sinus tissue is formed from an aerodigestive mucosa (e.g., a sinonasal mucosa or a mucosa from the gastrointestinal tract). In some embodiments, the SEM graft in the skull base and/or the SEM graft in the endogenous nasal tissue is formed from a bioengineered mucosal tissue graft. In some embodiments of any of the methods described herein, the SEM graft in the skull base is formed in the posterior frontal table, cribiform plate/ethmoid roof, planum sphenoidale, tuberculum, sella, clival recess, clivus, or cervical spine.

In some embodiments of any of the methods described herein, the at least one pharmaceutical agent or analgesic is formulated as a component of a biodegradable biocompatible polymer. In some embodiments of any of the methods described herein, the biodegradable biocompatible polymer is cationic. In some embodiments of any of the methods described herein, the biodegradable biocompatible polymer is a gel. In some embodiments, the gel is an alginate gel (e.g., sodium alginate), a cellulose-based gel (e.g., carboxymethyl cellulose or carboxyethyl cellulose), or a chitosan-based (e.g., chitosan glycerophosphate; see, e.g., Bleier et al., Am J Rhinol Allergy 23, 76-79, 2009) gel.

In some embodiments of the methods described herein, the pharmaceutical agent or analgesic is formulated as a liquid. In some embodiments of the methods described herein, the liquid is a thermosetting liquid. In some embodiments of all of the methods described herein, the at least one pharmaceutical agent or analgesic is administered in a volume of 8 mL or less. In some embodiments of the methods described herein, the pharmaceutical agent or analgesic is administered in a sustained-release formulation.

In some embodiments of the methods described herein, the pharmaceutical agent or analgesic has a molecular size of greater than 500 Daltons (e.g., greater than 1 kD, 5 kD, 10 kD, 15 kD, 20 kD, 25 kD, 30 kD, 70 kD, or 100 kD, up to about 500, 750, 1000, 1500, 2000, or 2500 kD, e.g., from 500 D to 500 kD, or from 500 D to 1000 kD), has a net negative or net positive charge, is a polar molecule, or any combination thereof. In some embodiments of all of the methods described herein, the at least one pharmaceutical agent is selected from the group of: a chemotherapeutic agent, L-DOPA, carbidopa, an anti-depressant agent, an anti-psychotic agent, donepezil, rivastigmine tartrate, galantamine, memantine, ISIS-SOD1, ISIS-SMN, ISIS-TTR, ELND005, β- or γ-secretase inhibitors, neurotrophic peptides (e.g., glial cell-derived neurotrophic factor), nanoparticles, fusion proteins, and viral vectors.

In some embodiments of any of the methods described herein, the neurological disorder is selected from the group of: Parkinson's disease, Alzheimer's disease, frontotemporal dementia, a brain cancer (e.g., glioblastoma multiforme, oligodendroglioma, astrocytoma, oligogastrocytoma, ependymoma, medulloblastoma, and meningioma), Huntington's disease, Bell's palsy, stroke, epilepsy, migraine, a sleep disorder, multiple sclerosis, muscular dystrophy, amyotrophic lateral sclerosis, acute disseminated encephalomyelitis, encephalitis, Creutzfeldt-Jakob disease, meningitis, depression, and schizophrenia.

In some embodiments of any of the methods described herein, the administering results in a decrease (e.g., an observable, detectable, or significant decrease) in the number or the severity, frequency, or duration of one or more symptoms of the neurological disorder. In some embodiments of the methods described herein, the administering results in a decrease (e.g., an observable, detectable, or significant decrease) in the severity, frequency, or duration of pain (e.g., pain score) in a subject.

Also provided herein are biocompatible endonasal reservoir devices that contain a section of tubing (e.g., catheter tubing) that is connected to a body, where the body has the capacity to contain a volume of a (e.g., at least one) pharmaceutical composition and contains an (e.g., at least one) opening or permeable surface, the opening or permeable surface is capable of releasing the pharmaceutical composition from the body, and the device is dimensioned to fit within an endogenous sinus tissue of the subject. In some embodiments, the tubing has an inner diameter between about 0.2 mm and about 5 mm. In some embodiments, the tubing has a length between about 1.0 cm and about 15 cm. In some embodiments, the end of the tubing that is not connected to the body is closed with a resealable material (e.g., a material containing silicone).

In some embodiments, the body is conical frustrum-shaped, spherical, rectangular, tubular, or ellipsoidal. In some embodiments, the body contains an expandable polymer material. In some embodiments, the body has the capacity to contain a volume of 8 mL or less. In some embodiments, the body contains an (e.g., at least one) opening (e.g., at least one opening with a diameter equal to or less than 1.0 $cm^2$). In some embodiments, the body contains a (e.g., least one) permeable surface (e.g., at least one permeable surface with an area equal to or less than 3.0 $cm^2$).

As used herein, the term "delivering" is meant providing a therapeutically effective amount of at least one pharmaceutical agent or composition to a subject.

By the phrase "therapeutically effective amount" is meant a dose of a pharmaceutical agent or composition that is sufficient to provide an observable or detectable beneficial physical effect (e.g., an effect that can be detected, observed, or measured) in a subject. In some embodiments, a therapeutically effective amount of a pharmaceutical agent decreases (e.g., a significant, detectable, or observable decrease) in the number or the severity, duration, or frequency of one of more (e.g., two, three, four, or five) symptoms of a disease (e.g., a neurological disorder) in a subject. In some embodiments, a therapeutically effective amount of an analgesic decreases (e.g., a significant, detectable, or observable decrease) in the severity, duration, or frequency of pain (e.g., pain score) in a subject.

By the term "pharmaceutical agent" is meant any molecule (e.g., protein (e.g., an antibody, antigen-binding fragment of an antibody, or a derivative or conjugate thereof), nucleic acid, lipid, carbohydrate, or small molecule (e.g., inorganic, organic, or mixed inorganic-organic molecule), or combination thereof) that is administered to a subject in order to achieve a therapeutic effect. Non-limiting methods of administration of pharmaceutical agents are described herein and are known in the art. Non-limiting examples of formulations of pharmaceutical agents are described herein and are known in the art. In some embodiments, the administration of at least one pharmaceutical agent results in a decrease (e.g., a significant, detectable, or observable decrease) in the number or the severity, frequency, or duration of one or more symptoms of disease (e.g., a neurological disorder) in a subject. In some embodiments, the administration of at least one pharmaceutical agent (e.g., an analgesic) results in a decrease (e.g., a significant, detectable, or observable decrease) in the severity, frequency, or duration of pain (e.g., pain score) in a subject. A wide variety of pharmaceutical agents are known in the art and are described herein.

By the term "analgesic" is meant any molecule that decreases pain in a subject. Non-limiting examples of analgesics are described herein. Additional examples of analgesics are known in the art.

By the term "central nervous system" is meant the brain, the spinal cord, the cerebral spinal fluid (CSF) that surrounds the brain and the spinal cord, and their associated linings (dura, arachnoid, pia mater, and choroid plexus).

By the term "directly administering" is meant placing at least one pharmaceutical agent (e.g., formulated as a component of a solid (e.g., a powder or polymer), liquid (e.g., a thermosetting liquid), or gel (e.g., a cationic polymer or any of the polymers described herein)) onto a specific tissue surface (e.g., a SEM graft in the skull base of a subject), into a specific tissue space (e.g., an endonasal reservoir), or into an endonasal reservoir device in a subject.

By the term "skull base" is meant the bony interface between the anterior, middle, or posterior cranial fossae and the tissue structures immediately inferior to them. The air-filled sinonasal cavity is situated adjacent to regions of the anterior, middle, or posterior cranial fossae. The skull base is formed from several layers including the nasal mucosa, mucoperiosteal layer, the bony layer of the skull base, the intracranial dura, and the arachnoid layer, with the arachnoid layer abutting the intracranial environment (the subarachnoid space). The skull base contains a number of individual subsites extending from the posterior wall of the frontal sinus through the clivus, including the cervical spine. From the anterior to posterior direction, these subsites include: the posterior frontal table, cribiform plate/ethmoid roof, planum sphenoidae, tuberculum, sella, clival recess, or clivus. The lateral limits of the skull base include the lateral extent of the frontal, ethmoid, or sphenoid sinuses. These anatomical structures are known in the art and are further described herein.

By the term "semipermeable epithelial membrane" or "SEM" is meant an epithelial tissue (e.g., a heterologous or autologous epithelial tissue) that has an increased (e.g., a detectable, measurable, or significant increase) permeability for specific classes of molecules (e.g., any of the pharmaceutical agents described herein) compared to the permeability of the blood-brain-barrier (BBB) for the same classes of molecules. In some embodiments, the SEM has increased permeability for at least one pharmaceutical agent that has a molecular size of greater than 500 Da (e.g., greater than 600 Da, 700 Da, 800 Da, 900 Da, 1 kDa, 2 kDa, 3 kDa, 4 kDa, 5 kDa, 10 kDa, 20 kDa, 30 kDa, 70 kD, or 100 kD), has a net positive or net negative charge, or is a polar molecule compared to the permeability of the BBB for the same at least one pharmaceutical agent. The permeability of a SEM can be determined using methods described herein. Additional methods for determining the permeability of a SEM are known in the art. Non-limiting examples of SEMs include: sinonasal mucosa, such as nasoseptal epithelial tissue, middle and inferior turbinate epithelial tissue, anterior septal epithelial tissue, as well as palatal epithelial tissue. Additional non-limiting examples of SEMs are mucosa from the gastrointestinal tract and bioengineered mucosa membranes. Additional examples of SEMs are known in the art.

In some embodiments, the SEM can be vascularized (e.g., contains at least one artery or is pedicled on branches of the external or internal carotid artery system). In some embodiments, the SEM is a nasoseptal epithelial tissue that contains at least one artery. In some embodiments the SEM may be composed of a free tissue graft comprised of any epithelial or endothelial layer or sheet of tissue. One or more SEMs can be used to form one or more grafts in the skull base of a subject and/or one or more SEMs can be used to form one or more grafts in an endogenous sinus tissue in a subject. Any combination of two or more SEMs can be used in the methods described herein.

By the phrase "SEM graft in the skull base" is meant a structure resulting from a procedure including the removal of a portion of the sinonasal (and/or olfactory) mucosa, mucoperiosteal layer, and the bony layer in the skull base of a subject, an incision in, removal, or displacement of a portion of the intracranial dura and the arachnoid layer in the skull base of the subject, and the replacement of the excised intracranial dura and arachnoid layer or placing into or over the incision in the intracranial dura and arachnoid layer a SEM (e.g., any of the SEMs described herein). The SEM graft in the skull base can be located in the roof of the sphenoid sinus (e.g., in the planum sphenoidale, tuberculum, or a sella subsite). Additional sites for the formation of the SEM graft in the skull base are described herein.

By the term "blood-brain-barrier" or "BBB" is meant a layer of cells that are physically connected by tight junctions, which surround the CNS and restrict or prevent the passage of molecules or infectious agents to the CNS. In the lining of the brain (dura and arachnoid) which is directly apposed to the skull base, the blood-brain-barrier is located in the arachnoid layer. For example, the blood-brain-barrier restricts or prevents the passage of molecules greater than 500 Da, molecules with a net positive or net negative charge, or polar molecules to the CNS (e.g., the brain or the spinal cord).

By the term "endonasal reservoir" is meant a surgically generated anatomical site having the capacity to contain a volume of a (e.g., at least one) one pharmaceutical composition (e.g., a composition containing at least one pharmaceutical agent, such as any of the polymer gels described herein) that is defined, in part, by at least two structures or surfaces: (i) a SEM graft in the skull base (as described herein), and (ii) a SEM graft in or over an endogenous sinus tissue or in a position proximal to the SEM graft in the skull base. In some embodiments, the space between or bordered by the SEM graft in the endogenous sinus tissue and the SEM graft in the skull base includes a pre-existing sinus lumen.

By the term "endonasal reservoir device" is meant a three-dimensional biocompatible, synthetic construct that has a section of tubing (e.g., catheter tubing with an inner diameter of between 0.2 mm to 5 mm) that is connected to a body (e.g., a conical frustrum-shaped, spherical, rectangular, tubular, or ellipsoidal body) that has the capacity to contain a volume (e.g., 8 mL or less) of a (e.g., at least one) pharmaceutical composition (e.g., a composition containing at least one pharmaceutical agent, such as any of the polymer gels described herein), where the expandable body has an (e.g., at least one) opening (e.g., an opening with a diameter equal to or less than 1.0 $cm^2$) or a permeable surface (e.g., area equal to or less than 3.0 $cm^2$) through which the pharmaceutical composition can be released from the interior of the body onto a SEM graft in the skull base of a subject. In some embodiments, the body can be made of an expandable material. The body is dimensioned such that it fits comfortably within the endogenous sinus tissue of a subject. In embodiments where the body is made of an expandable material, the body is designed such that the fully-expanded body (i.e., the body filled to capacity with the pharmaceutical composition) fits comfortably in the endogenous sinus tissue of a subject.

The tubing should have a length sufficient to connect the body (placed in an endogenous sinus tissue of a subject) to the sphenoid sinus in the subject (e.g., between 1.0 cm to 15 cm in length). The end of the tubing that is not connected to the body can be closed with a resealable material (e.g., a polymer or material containing silicon) that can be punctured by a needle. Endonasal reservoir devices can be constructed using any of the polymers described herein and any polymers known in the art. Non-limiting additional features and aspects of endonasal reservoir devices are described herein.

By the term "expandable polymer material" is meant an elastic material that is capable of increasing its surface area upon application of force (e.g., hydrodynamic force). In some embodiments, an expandable polymer material forms an enclosed three-dimensional shape, where the introduction of a volume of a substance (e.g., liquid, gel, or solid pharmaceutical composition) into the lumen or interior of the three-dimensional shape results in an increase in the total surface area of the polymer material (i.e., results in an increase in the total volume of the three-dimensional shape). Non-limiting examples of expandable polymer materials are described herein and additional examples are known in the art.

By the term "neurological disorder" is meant any disease or condition that affects the CNS (e.g., the brain or the spinal cord). In some embodiments, the neurological disorder has one of more of the following features: unregulated or misregulated cell growth, increased neuronal cell death, increased loss of myelin, pathological protein misfolding and/or aggregation, a pathological increase or decrease in neurohormone or neurotransmitter production or turn-over, a pathological increase or decrease in neurohormone or neurotransmitter receptor activity, a pathological increase or decrease in synaptic transmission between neurons, and a pathological increase or decrease in neuronal intracellular signaling pathways. In some embodiments, a neurological disorder can also be manifested by one or more of the following symptoms: forgetfulness, confusion, difficulty speaking, loss of memory, disorientation, difficulty writing, depression, anxiety, social withdrawal, mood swings, irritability, sleeping problems (e.g., insomnia), wandering, tremor, slowed motion (bradykinesia), rigid muscles, impaired posture or balance, muscle weakness, loss of coordination, headache, seizures, nausea, double vision or blurred vision, lethargy, and overeating or appetite loss. Non-limiting examples of neurological disorders are known in the art and are described herein.

By the term "endogenous sinus tissue" is meant a tissue present in the sinus of a subject that is proximal to the skull base of the subject. Endogenous sinus tissue includes, without limitation, the tissues present in the maxillary sinuses, the frontal sinuses, the ethmoid sinuses, and sphenoid sinuses, as well as the nasal cavity including but not limited to the septum, nasal floor, inferior, middle, and superior turbinates.

By the term "endogenous sinus tissue surface" is meant a surface of a tissue present in the sinus that is proximal (e.g., anterior to or opposite of) to a SEM graft in the skull base (as described herein). In some embodiments, the endogenous sinus tissue surface is proximal to a SEM graft present in the planum sphenoidale, tuberculum, or a sella subsite.

By the term "roughly parallel" is meant the positioning of two separate linear or approximately-linear (e.g., curved) tissue structures or surfaces (e.g., in a subject) such that one of the tissue structures or surfaces faces or is opposite of (e.g., inferior or anterior) the other tissue structure. In some embodiments, one of the two tissue structures or surfaces is an SEM graft in the skull base and the second of the two tissue structures or surfaces is a SEM placed in an endogenous sinus tissue.

By the term "proximal" is meant the positioning of two structures or surfaces (e.g., an SEM graft in the skull base and an SEM graft in an endogenous sinus tissue surface, or an SEM graft in the skull base and an endonasal reservoir device) such that they are within a close distance of each other (e.g., one point in the first structure or surface and one point in the second structure or surface are within at least 6.0 cm, 5.5 cm, 5.0 cm, 4.5 cm, 4.0 cm, 3.5 cm, 3.0 cm, 2.0 cm, 2.5 cm, 2.0 cm, 1.5 cm, 1.0 cm, 0.8 cm, 0.6 cm, 0.5 cm, 0.4 cm, 0.3 cm, 0.2 cm, or 0.1 cm of each other).

By the term "endoscopic procedure" is meant a procedure that is performed, in part, through the use of instrument that allows the examination or manipulation of tissues in the interior of a hollow organ or cavity in the body of a subject. In some embodiments, an endoscopic procedure is performed to place an SEM graft in the skull base of a subject. In some embodiments, an endoscopic procedure is performed to place a SEM graft over endogenous sinus tissue or in a position proximal (e.g., roughly parallel) to the SEM graft in the skull base. In some embodiments, the endoscopic procedure involves the removal of portion of the nasal mucosa, mucoperiosteal layer, and the bony layer from the skull base of a subject, and an incision in or removal of a portion of the intracranial dura and the arachnoid layer in the skull base of a subject. In some embodiments, an endoscopic procedure is performed to resect a SEM (e.g., an autologous SEM, e.g., any of the SEMs described herein) from a subject. An endoscopic procedure can also be used to administer at least one pharmaceutical agent or composition onto an SEM graft in the skull base of a subject, into an endonasal reservoir, or into a endonasal reservoir device in a subject. Any of the methods described herein can be performed through an endoscopic procedure.

By the term "interfacial procedure" is meant a procedure that is performed, in part, through at least one incision or puncture in the facial tissue of a subject. In some embodiments, an interfacial procedure is performed to place an SEM graft in the skull base of a subject. In some embodiments, an interfacial procedure is performed to place a SEM graft over an endogenous sinus tissue or in a position proximal (e.g., roughly parallel) to the SEM graft in the skull base or to place an endonasal reservoir device in an endogenous sinus tissue in a subject. In some embodiments, the interfacial procedure involves the removal of portion of the nasal mucosa, mucoperiosteal layer, and the bony layer, and an incision in or removal of a portion of the intracranial dura and the arachnoid layer in the skull base of a subject. In some embodiments, an interfacial procedure is performed to resect a SEM (e.g., an autologous SEM, e.g., any of the SEMs described herein) from a subject (e.g., a SEM from the nasoseptal flap). An interfacial procedure (e.g., injection) can also be used to administer at least one pharmaceutical agent or composition onto an SEM graft in the skull base of a subject or into an endonasal reservoir or endonasal reservoir device in a subject. Any of the methods described herein can be performed through an interfacial procedure.

By the term "intracranial procedure" is meant a procedure that is performed, in part, through at least one incision or puncture in the cranium of a subject.

By the term "sinonasal mucosa" is meant a mucous membrane that lines the sinonasal passage in a subject (e.g., a human).

By the term "biodegradable" is meant a composition (e.g., a molecule or polymer (e.g., a gel polymer)) that naturally decomposes in a tissue in a subject (e.g., human). In some embodiments, a biodegradable composition does not result in the formation of a precipitate in a tissue in the subject (e.g., the products of the decomposition are naturally cleared from the tissue in which the biodegradable composition is placed, e.g., by mucocilliary clearance) or in an endonasal reservoir device placed in a subject. In some embodiments, the products of the decomposition are excreted by the subject. In some embodiments, the biodegradable composition is a sustained-release composition (e.g., a composition having an in vivo half-life of at least 3 days, 4 days, 5 days, 6 days, 7 days, 8 days, 10 days, 14 days, 21 days, 1 month, or 2 months).

By the term "biocompatible" is meant a composition (e.g., a molecule or polymer (e.g., a gel polymer)) that does not induce an observable or detectable immune response or inflammatory response in a subject. Methods for detecting an immune response or an inflammatory response in a subject are described herein. Additional methods for detecting an immune response or an inflammatory response in a subject are known in the art.

By the term "alginate gel" is meant a semi-solid composition containing at least one algal polysaccharide. A non-limiting example of an alginate gel is sodium alginate.

By the term "cellulose-based gel" is meant a semi-solid composition containing at least one form of cellulose. In non-limiting examples, the at least one form of cellulose can be carboxymethyl cellulose or carboxyethyl cellulose.

By the term "chitosan-based gel" is meant a semi-solid composition containing at least one linear polysaccharide containing β-(1,4)-linked D-glucosamine and N-acetyl-D-glucosamine. In one non-limiting embodiment, the chitosan-based gel can be chitosan glycerophosphate; see, e.g., Bleier et al., Am J Rhinol Allergy 23, 76-79, 2009.

By the term "thermosetting liquid" is meant a liquid composition that can undergo a phase transition to a solid or a semi-solid state (e.g., a gel) spontaneously or following exposure to some form of energy (e.g., vibrational, light, or heat energy). In some embodiments, the phase transition to a solid or semi-sold state can occur within a tissue (e.g., an endonasal reservoir) or in an endonasal reservoir device in a subject (e.g., a human). Non-limiting examples of thermosetting liquids are described herein. Additional examples of thermosetting liquids are known in the art.

By the term "sustained-release formulation" is meant a composition that is formulated to allow for the continued release of at least one pharmaceutical agent over a period of time. For example, a sustained-release formulation may allow for the release of at least one pharmaceutical agent over a period of at least 3 days, 4 days, 5 days, 6 days, 7 days, 2 weeks, 3 weeks, 1 month, or 2 months. In some embodiments, the sustained-release formulation may have an in vivo half-life of at least 3 days, 4 days, 5 days, 6 days, 7 days, 8 days, 10 days, 14 days, 21 days, 1-month, or 2 months. Examples of sustained-release formulations are described herein. Additional examples of sustained-release formulations are known in the art.

By the term "polar molecule" is meant a molecule that has a distribution of electrical charge(s) that results in an electric dipole or multipole moment. Molecular polarity is dependent on the difference in the electronegativity between the atoms present in a molecule and the asymmetry of the molecule's structure.

By the term "chemotherapeutic agent" is meant a molecule that can be used to reduce the rate of cancer cell growth or to induce or mediate the death (e.g., necrosis or apoptosis) of cancer cells in a subject (e.g., a human). In non-limiting examples, a chemotherapeutic agent can be a small molecule, a protein (e.g., an antibody, an antigen-binding fragment of an antibody, or a derivative or conjugate thereof), a nucleic acid, or any combination thereof. Non-limiting examples of chemotherapeutic agents include: cyclophosphamide, mechlorethamine, chlorabucil, melphalan, daunorubicin, doxorubicin, epirubicin, idarubicin, mitoxantrone, valrubicin, paclitaxel, docetaxel, etoposide, teniposide, tafluposide, azacitidine, axathioprine, capecitabine, cytarabine, doxifluridine, fluorouracil, gemcitabine, mercaptopurine, methotrexate, tioguanine, bleomycin, carboplatin, cisplatin, oxaliplatin, all-trans retinoic acid, vinblastine, vincristine, vindesine, vinorelbine, and bevacizumab (or an antigen-binding fragment thereof). Additional examples of chemotherapeutic agents are known in the art.

By the term "anti-depressant agent" is meant any molecule that can be used to decrease the number of symptoms or decrease the severity, duration, or frequency of one of more symptoms of depression or a personality/mood disorder in a subject. Non-limiting examples of anti-depressant agents include selective serotonin reuptake inhibitors (e.g., citalopram, escitalopram, fluoxetine, paroxetine, and sertraline), serotonin-norepinephrine reuptake inhibitors (e.g., desvenlafaxine, duloxetine, milnacipran, and venlafaxine), noradrenergic and specific serotonergic antidepressants (e.g., mianserin and mirtazapine), norepinephrine reuptake inhibitors (e.g., atomoxetine, mazindol, reboxetine, and viloxazine), norepinephrine-dopamine reuptake inhibitors (e.g., bupropion), selective serotonin reuptake enhancers (e.g., tianeptine), norepinephrine-dopamine disinhibitors (e.g., agomelatine), tricyclic antidepressants (e.g., amitriptyline, clomipramine, doxepin, imipramine, and trimipramine), secondary amine tricyclic depressants (e.g., desipramine, nortriptyline, and protripyline), monoamine oxidase inhibitors (e.g., isocarboxazid, moclobemide, phenelzine, selegiline, and tranylcypromine), buspirone, gepirone, nefazodone, trandospirone, trazodone, bupropion, benzodiazepines, amphetamine, methylphenidate, modafinil, lithium, carbamazepine, sodium valproate, and lamotrigine. Additional examples of anti-depressant agents are known in the art.

By the term "anti-psychotic agent" is meant any molecule that can be used to decrease the number of symptoms or decrease the severity, duration, or frequency of one of more symptoms of a psychotic disorder in a subject. Non-limiting examples of anti-psychotic agents include risperidone, olanzapine, and quetiapine. Additional examples of anti-psychotic agents are known in the art.

By the term "fusion protein" is meant a polypeptide sequence that contains a contiguous sequence of amino acids from at least two different endogenous polypeptides.

By the term "nanoparticle" is meant a composite material that has a diameter of between 2 nm and 100 nm in size. A variety of nanoparticles are known in the art and can be used to deliver a therapeutic agent (e.g., any of the therapeutic agents described herein) to a subject.

By the term "neurotrophic peptide" is meant a protein that has one or more of the following activities: promotes the growth of developing neurons, promotes the survival or developing neurons, promotes the initial development of neurons in the central nervous system or peripheral nervous system, and promote regrowth of damaged neurons. Non-limiting examples of neurotrophic peptides include neurotrophins, glial cell-line derived neurotrophic factor family ligands, and neuropoietic cytokines.

By the term "gene therapy vector" is meant any nucleic acid or recombinant virus used to deliver a nucleic acid to a cell in a subject. Non-limiting examples of gene therapy vectors include recombinant lentiviruses, flaviviruses, herpes viruses, retroviruses, and adenoviruses. Additional examples of gene therapy vectors are known in the art.

By the phrase "decrease in the number, frequency, duration, or severity of symptoms" is meant a detectable or observable decrease in the number of symptoms in a subject or a detectable or observable decrease in the recurrence of at least one symptom, decrease in the length of time that at least one symptom persists in a subject, or a decrease in the intensity of at least one symptom in a subject. Non-limiting examples of symptoms of neurological disorders are described herein. Additional examples of neurological disorders are known in the art.

By the phrase "decrease in the frequency, duration, or severity of pain" is meant a detectable or observable decrease in the recurrence of pain, decrease in the length of time of pain, or a decrease in the intensity of pain in a subject.

As used herein, a "subject" is a mammal, including a human and a domestic or farm animal (e.g., a horse, mouse, rabbit, pig, sheep, goat, or cow).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing (FIGS. 15, 17, and 19) executed in color. Copies of this patent or patent application publication with color drawings will be provided by the Office upon request and payment of the necessary fee.

FIG. 10A-C is two endoscopic images and one MRI image of a human subject during different stages of the formation of an SEM graft in the skull base. FIG. 10A shows an intranasal view of a human brain after removal of the bone and meninges in the skull base (dashed line). FIG. 10B is a intranasal view of the surgical site after placement of a SEM graft over the surgically created opening in the skull base. FIG. 1C is an MRI image with an arrow pointing to the site of the healed SEM overlying the subarachnoid space (the arrow tip indicates the regions depicted in FIGS. 10A and 10B).

FIG. 11 is a schematic diagram of the murine SEM model. In the model, the SEM graft (indicated as "SMM") is implanted over the CSF filled subarachnoid space following removal of the bone and underlying meninges containing the blood brain barrier.

FIG. 12 is a hematoxylin- and eosin-stained cross section of a murine model with a SEM graft healed to adjacent bone and meninges with the basolateral surface communicating with the subarachnoid space.

DETAILED DESCRIPTION

Figure 1:
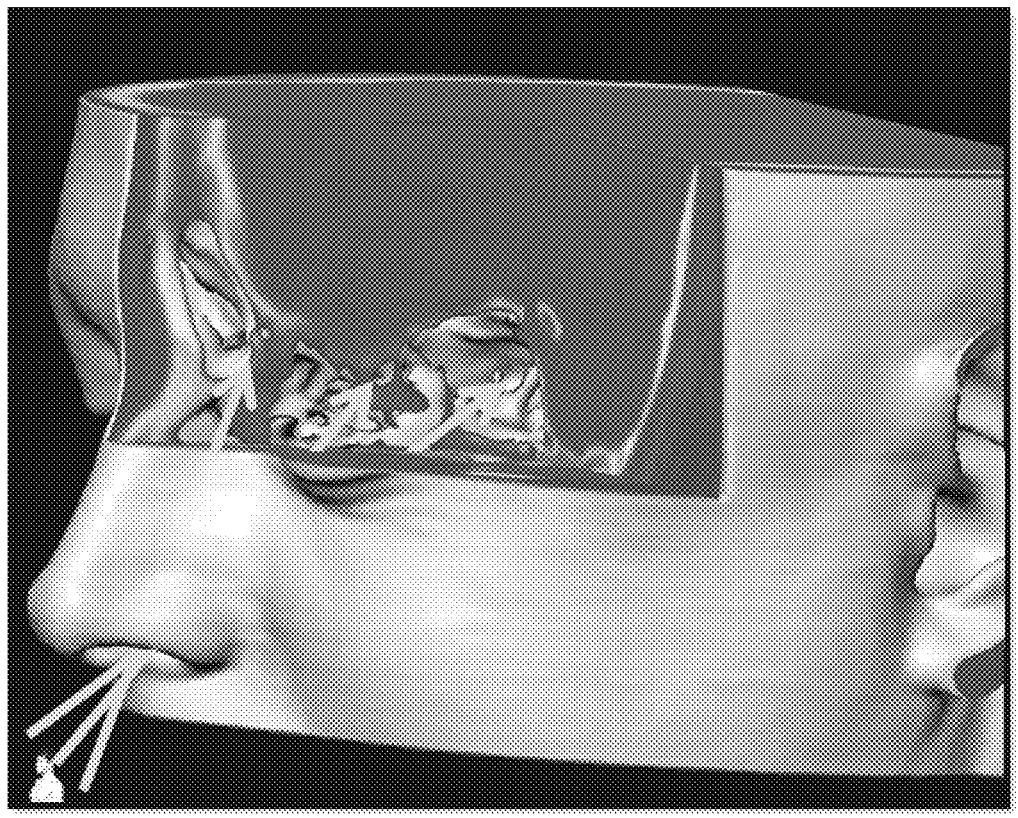
FIG. 1 is a diagram of the human skull indicating the three exemplary locations (arrows) for placing the SEM graft in the skull base.

The BBB restricts the ability of systemically administered (e.g., orally or parenterally administered) therapeutic agents to reach the CNS. Provided herein are methods of delivering pharmaceutical agents to the CNS of a subject, e.g., for treating a neurological disorder or pain in a subject.

The methods described herein provide several advantages over the systemic delivery of pharmaceutical agents for the treatment of neurological disorders or pain. These advantages can include one or more of: a decrease in the toxicity or adverse side effects observed in non-targeted tissue (e.g., tissues outside of the CNS) that result from systemic delivery of pharmaceutical agent(s), a reduction in the number of spikes in the dosage of pharmaceutical agents delivered to the CNS (e.g., a reduction in pulsatile dosing), an increase in the dosage of pharmaceutical agent(s) that can be administered to the subject without incurring toxicity or adverse side effects, an increase the in vivo (e.g., levels of pharmaceutical agent(s) in the CNS (e.g. in the CSF) of a subject, an increase in the efficiency of delivery of pharmaceutical agent(s) to the CNS of a subject, and an absence of or a reduction in immunological or inflammatory response to compositions containing at least one pharmaceutical agent (e.g., compared to systemically administered drugs or implants).

Methods of Forming a SEM Graft in the Skull Base

The methods of delivering at least one pharmaceutical agent to the CNS of a subject and the methods of treating neurological disorders or pain described herein utilize or are performed in a subject having a SEM graft in their skull base, an endonasal reservoir, or a SEM graft in their skull base and an endonasal reservoir device. Methods of forming a SEM graft in a skull base of a subject, forming an endonasal reservoir, and placing an endonasal reservoir device in a subject's endogenous sinus tissue are described below. The formation (or placement) of a SEM graft in the skull base, an endonasal reservoir, or a SEM graft and an endonasal reservoir device in a subject allows for the delivery of at least one (e.g., two, three, or four) pharmaceutical agent through a SEM graft in the skull base to the CNS.

General Description of Methods

The methods of forming an SEM graft into the skull base of a subject generally include: removing a portion of the nasal mucosa (and/or olfactory mucosa), mucoperiosteal layer, and the bony layer of the skull base of a subject; making an incision in the intracranial dura and the arachnoid layer in the skull base of the subject; making an incision in and removing or reflecting a position of the intracranial dura and the arachnoid layer in the skull base of the subject; and placing over the incision of the intracranial dura and the arachnoid layer a SEM. In some embodiments, the SEM graft in the skull base is formed by: removing a portion of the nasal mucosa, mucoperiosteal layer, and the bony layer of the skull base of a subject; removing a portion of the intracranial dura and the arachnoid layer; and replacing the excised intracranial dura and arachnoid layer with a SEM. The resulting SEM graft in the skull base has a basolateral side that communicates with the cerebrospinal fluid (CSF) compartment (also known as the subarachnoid space) or directly with the brain parenchyma.

The methods of forming an SEM graft in the skull base of a subject described herein can be performed, e.g., via an endoscopic transnasal procedure, by an interfacial procedure (making at least one puncture or incision into the facial tissue of the subject), or by an intracranial procedure (making at least one puncture or incision into the cranium of the subject). In some embodiments, the endoscopic transnasal procedure can be performed using a rigid or a flexible endoscope introduced through a nostril to allow for simultaneous visualization, magnification, and illumination of the surgical site. The surgical site may be visualized directly through the eyepiece of the endoscope; however, a digital camera may also be coupled to the endoscope to allow for projection of an image of the tissue site (e.g., a nasal or sinus tissue) onto a video monitor. Instrumentation can be introduced into the ipsilateral or contralateral nostril of the patient (e.g., by the same person or a second person) to allow for tissue manipulation (as described in detail below) under direct endoscopic view.

Some embodiments of these methods further include forming an endonasal reservoir by introducing a SEM graft over an endogenous sinus tissue or in a position proximal (e.g., roughly parallel) to the SEM graft in the skull base. The resulting endonasal reservoir allows for the storage and delivery of at least one pharmaceutical agent or a composition containing at least one pharmaceutical agent onto the SEM graft in the skull base. The endonasal reservoir provides an accessible site for redosing (e.g., one or more doses of at least one of any of the pharmaceutical compositions described herein) and drainage of degradation products of the at least one pharmaceutical agent or the composition containing at least one pharmaceutical agent (e.g., natural mucocilliary clearance or by lavage of the endonasal reservoir).

In some embodiments, an endonasal reservoir device is placed in an endogenous sinus tissue of a subject with a SEM graft in their skull base. As described in detail herein, an endonasal reservoir device contains a section of tubing (e.g., catheter tubing) that is connected to a body. The tubing has a length sufficient to extend from the sphenoid sinus to the body of the device located in an endogenous sinus tissue of the subject. The body is dimensioned so as to contain a volume of at least one pharmaceutical composition and contains at least one opening or permeable surface that allows the release of at least one pharmaceutical composition onto the SEM graft in the skull base of the subject. Following placement of the device, the at least one opening or permeable surface of the body is proximally located to the SEM graft in the skull base. Additional structural and functional features of endonasal reservoir devices are described herein.

All of the methods described herein can be performed to or on a subject without adversely affecting sinonasal health and function (e.g., without sinus or nasal blockage, infection, or inflammation).

Preparation of the Skull Base and Placement of the SEM

Figure 2:
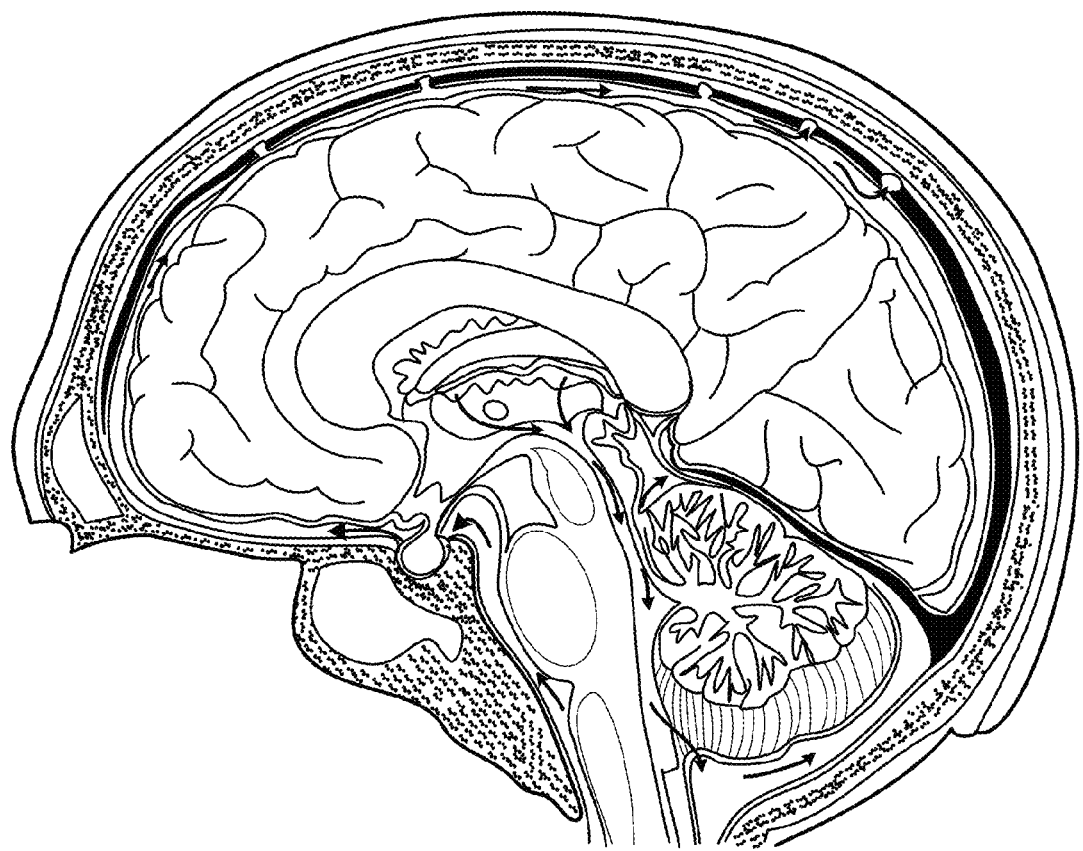
FIG. 2 is a diagram of the human skull indicating the CSF circulation pathway (small black arrows) and exemplary locations in the skull base for placing the SEM graft (thick black lines) near the beginning of the CSF circulation pathway (large black arrow).

The skull base (or cranial base), as is known in the art, is the bony interface between the anterior, middle, or posterior cranial fossae and the structures immediately inferior to them. The air-filled sinonasal cavity is situated adjacent to regions of the anterior, middle, or posterior cranial fossae. Any of these three regions of the skull base (e.g., the anterior, middle, or posterior cranial fossae) can be used as the site for forming the SEM graft in the skull base (FIG. 1). In some embodiments, the SEM graft in the skull base is formed at a location in the skull base proximal to the beginning of the cerebrospinal fluid (CSF) circulation pathway (FIG. 2; large black arrow). The SEM can be resected from another tissue in the subject (e.g., a pedicled nasoseptal flap from the tissues shown in FIG. 3). See, e.g., Chiu and Dunn, Otolaryngol Head Neck Surg. 2006 January; 134(1): 33-6, incorporated herein by reference.

The endogenous skull base contains several layers that act to impede the delivery of pharmaceutical agents from the intranasal cavity to the CNS. These layers include the nasal mucosa with its associated mucoperiosteal layer and/or olfactory mucosa, the bony layer of the skull base, the intracranial dura, and the arachnoid layer (which contains the BBB). Using a variety of instruments designed for intranasal use, these layers can be resected while maintaining hemostasis. The resection can also be performed by an interfacial procedure or an intracranial procedure. The areas of the skull base where tissue resection can be performed include any individual or combination of subsites extending from the posterior wall of the frontal sinus through the clivus, including the cervical spine. Going from the anterior to posterior direction, the potential subsites include the posterior frontal table, the cribiform plate/ethmoid roof, planum sphenoidale, tuberculum, sella, clival recess, or clivus. The lateral limits of the sites for the placement of the SEM include the lateral extent of the frontal, ethmoid, or sphenoid sinuses.

Figure 4:
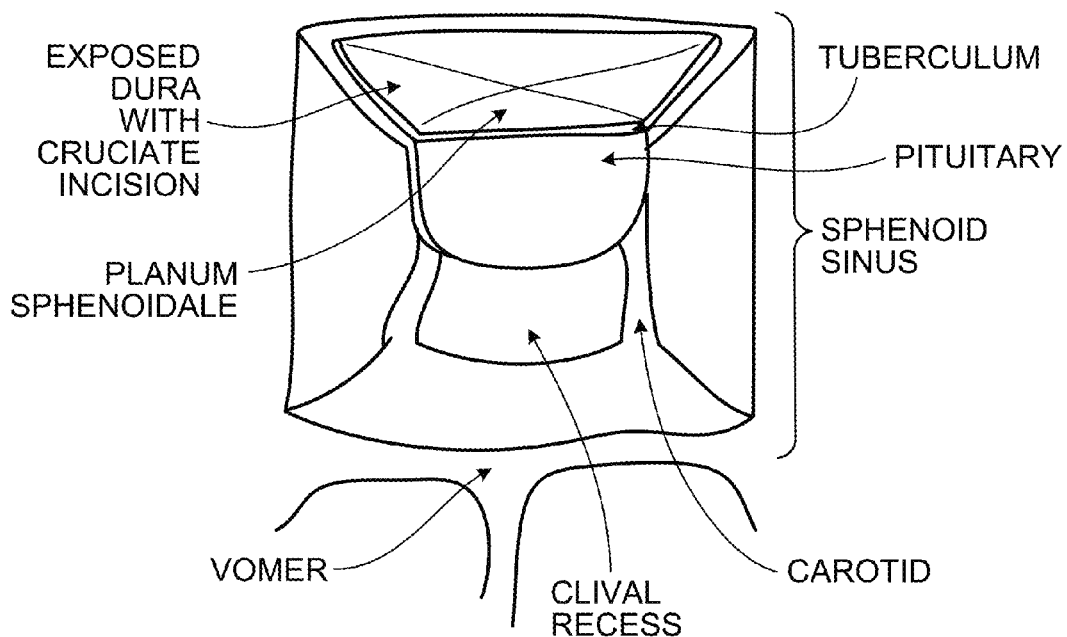
FIG. 4 is a diagram showing a cruciate incision made in the intracranial dura and arachnoid layer following removal of the nasal mucosa, mucoperiosteal layer, and the bony layer from a section of the skull base within the sphenoid sinus.
Figure 5:
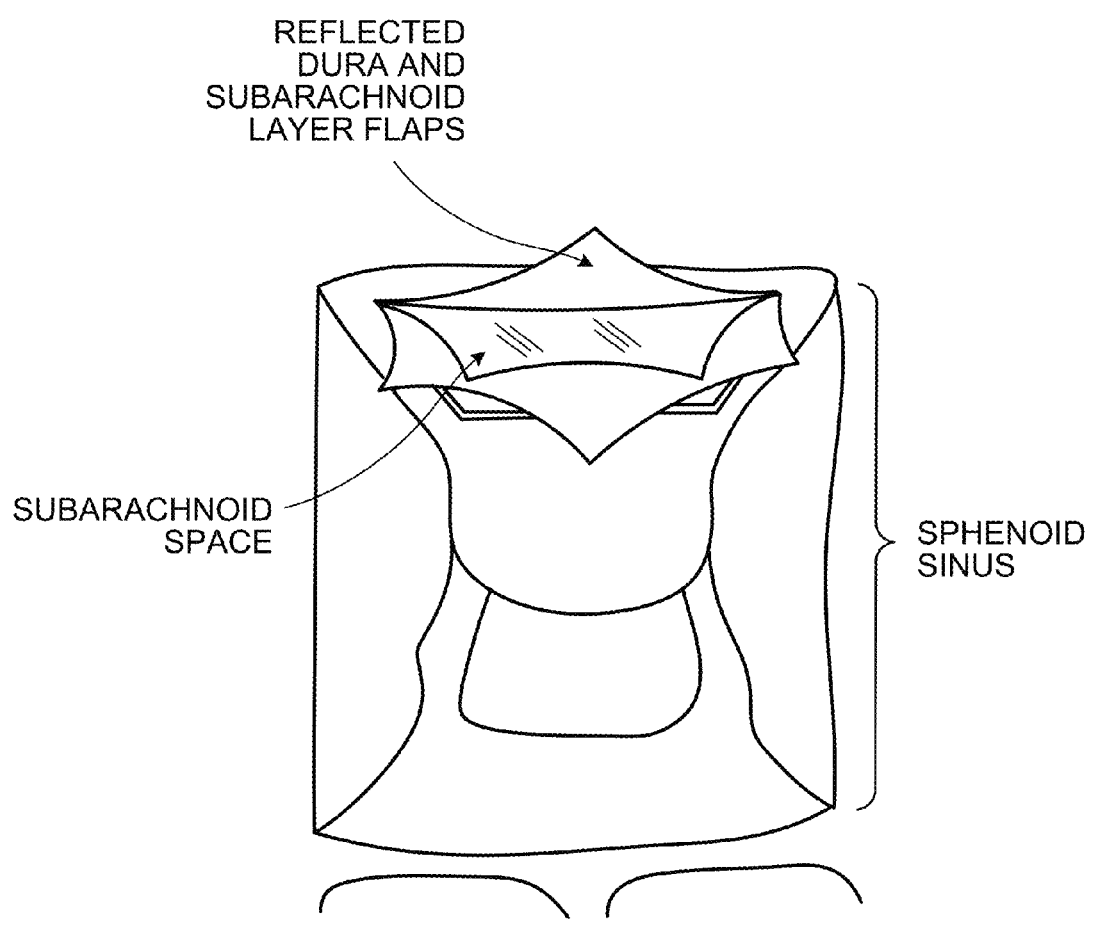
FIG. 5 is a diagram showing the reflection of the flaps of intracranial dura and arachnoid layer following a cruciate incision made in the intracranial dura and arachnoid layer. The reflection of these flaps allows access to the subarachoid space while preventing postoperative arachnoid regrowth.

Following removal of a portion of the nasal mucosa (and/or olfactory mucosa), the mucoperiosteal layer, and the bony layer of the skull base (e.g., equal to or less than 0.5 $cm^2$, 1 $cm^2$, 1.5 $cm^2$, 2 $cm^2$, 2.5 $cm^2$, 3 $cm^2$, 3.5 $cm^2$, 4 $cm^2$, 4.5 $cm^2$, 5 $cm^2$, 6 $cm^2$, 7 $cm^2$, 8 $cm^2$, 10 $cm^2$, 12 $cm^2$, 14 $cm^2$, 16 $cm^2$, 18 $cm^2$, 20 $cm^2$, 22 $cm^2$, or 25 $cm^2$), a section of the intracranial dura and arachnoid layer can be removed (e.g., equal to or less than 0.5 $cm^2$, 1 $cm^2$, 1.5 $cm^2$, 2 $cm^2$, 2.5 $cm^2$, 3 $cm^2$, 3.5 $cm^2$, 4 $cm^2$, 4.5 $cm^2$, 5 $cm^2$, 6 $cm^2$, 7 $cm^2$, 8 $cm^2$, 10 $cm^2$, 12 $cm^2$, 14 $cm^2$, 16 $cm^2$, 18 $cm^2$, 20 $cm^2$, 22 $cm^2$, or 25 $cm^2$) or at least one (e.g., two, three, or four) incision (e.g., equal to or less than 0.25 cm, 0.5 cm, 0.75 cm, 1.5 cm, 2 cm, 2.5 cm, 3 cm, 3.5 cm, 4 cm, 4.5 cm, 5 cm, 6 cm, 7 cm, or 8.0 cm) in both the intracranial dura and arachnoid layer can be made. In some embodiments, a cruciate incision is made in the intracranial dura and arachnoid layer (FIG. 4), and the four sections of tissue (flaps) can be reflected (folded back) prior to the placement of the SEM into the created opening in the intracranial dura and arachnoid layer (FIG. 5). Likewise, in some embodiments three or more incisions can be made in star-like pattern and the resulting sections of tissue (flaps) can be reflected (folded back) prior to the placement of the SEM into the created opening in the intracranial dura and arachnoid layer. The use of a cruciate- or star-like incision with dural/arachnoid reflection prevents regrowth of the blood-brain barrier in the subject.

In some embodiments, a section of the intracranial dura and the arachnoid layer is removed, and the SEM is placed into the created opening in the intracranial dura and arachnoid layer. In some embodiments of these methods, packing or a sponge-like material is placed over/in the incision or the opening in the intracranial dura and arachnoid layer prior to placement of the SEM graft in the incision or opening.

The removal of the nasal mucosa (and/or olfactory mucosa), the mucoperiosteal layer, and the bony layer of the skull base (described herein), and the incision in or removal of a portion of the intracranial dura and the arachnoid layer (described herein), results in a defect or opening in the BBB that allows communication between the subarachnoid space and the sinonasal space. The SEM is placed in this defect or opening should be watertight in order to prevent the leakage of CSF into the sinonasal cavity following the procedure. In order to avoid leakage of CSF, the SEM is preferably placed over the defect or opening in the intracranial dura and the arachnoid layer such that the SEM fully overlaps all the boundaries of the defect or opening in the intracranial dura and the arachnoid layer. The methods described herein can further include the placement of an underlay graft within the epidural space; however, this graft must also have an increased permeability for at least one pharmaceutical agent (e.g., pharmaceutical agents with a size greater than 500 Da or a net positive or net negative charge, or polar pharmaceutical agents) compared to the permeability of the BBB to the same at least one pharmaceutical agent. The methods described herein can further include the placement of an absorbable or non-absorbable nasal packing (e.g., a sponge, dressing, or balloon) over the SEM graft in the skull base following its placement in the defect or opening in the intracranial dura and the arachnoid layer. In some embodiments the nasal packing is placed over the SEM graft in the skull base for at least 1 day, 2 days, 3 days, 4 days, 5 days, 6 days, 1 week, 2 weeks, 3 weeks, or 1 month after the SEM has been placed into the incision or opening in the intracranial dura and arachnoid layer.

In some embodiments, more than one SEM graft can be formed in the skull base of the subject. For example, a SEM graft in the skull base can be formed on each side of the subject's face.

SEMs

As described herein, a SEM is placed in an opening or incision in the intracranial dura and the arachnoid layer. In some embodiments, the SEM has one or more of the following features: it has robust wound healing properties that allow for the water-tight and immunocompetent resealing of the defect or opening in the arachnoid layer and the intracranial dura; it does not induce a local (e.g., endonasal) or systemic inflammatory or immunological response in the subject; and it maintains its advantageous semipermeable characteristics (e.g., increased permeability to at least one pharmaceutical agent as compared to the permeability of the same at least one pharmaceutical agent in the BBB) that allow for diffusion of at least one pharmaceutical agent from the sinonasal compartment to the CNS (e.g., into the subarachnoid space). In all of the methods described herein, it is important that the SEM has increased permeability to at least one pharmaceutical agent as compared to the permeability of the same at least one pharmaceutical agent in the BBB.

Figure 3:
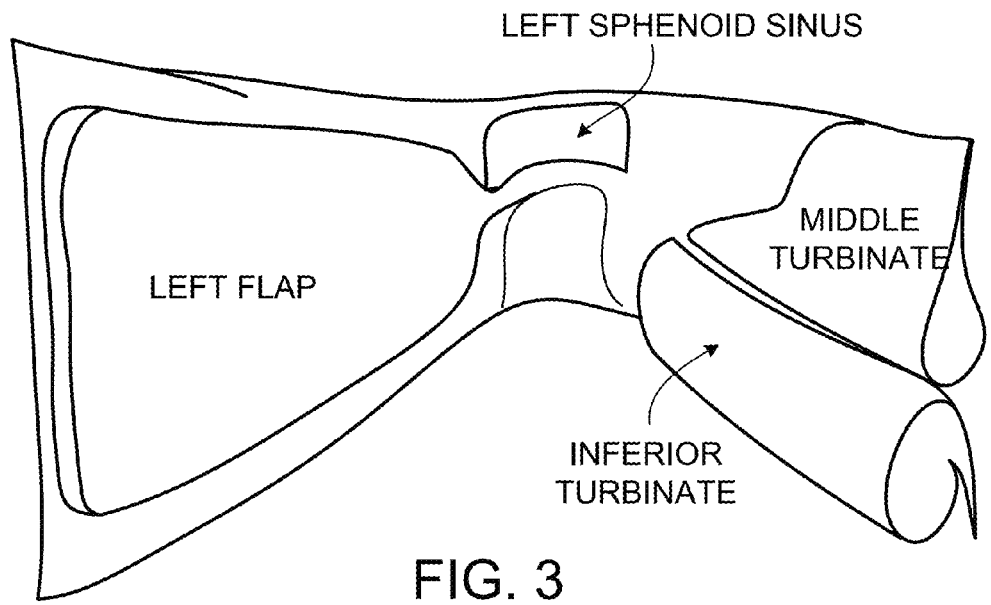
FIG. 3 is a diagram depicting a pedicled nasoseptal flap which may comprise the SEM. A SEM can be harvested, for example, from the middle turbinate and the inferior turbinate.

An SEM can be derived from the same subject (i.e., an autologous SEM), from a different human subject (e.g., a heterologous SEM), or from an animal (e.g., a xenogenous SEM). In some embodiments, the SEM is an autologous SEM (e.g., from the sinonasal mucosa of the same subject). A number of different tissues (e.g., epithelial tissues) can be used as an SEM. In some embodiments, the SEM can be a free, pedicled, or microvascular anastomosed flap of tissue. In some embodiments, the SEM is a section of pedicled sinonasal mucosa. In some embodiments, the SEM is formed from a gastrointestinal mucosa or a tissue engineered mucosa. Sinonasal mucosa is known to be several orders of magnitude more permeable than the BBB. SEMs formed from sinonasal mucosa can be pedicled on branches of the external or internal carotid artery system and can contain at least one (e.g., two, three, or four) artery. Non-limiting examples of SEMs formed from sinonasal mucosa include a section of mucosa from the nasoseptum, the middle and inferior turbinate, and the anterior septum. In some embodiments, the SEM is formed from epithelial mucosa from the palate. In desirable embodiments, the SEM is formed from nasoseptal mucosa (also described as a nasoseptal flap; FIG. 3) which is pedicled on the nasoseptal artery. An SEM formed from a nasoseptal flap can have a large surface area and a relatively small amount of transmembrane efflux proteins (e.g., P-glycoprotein) which can provide for enhanced permeability of at least one pharmaceutical agent (relative to the permeability of the same at least one pharmaceutical agent in the BBB).

The area of an SEM (e.g., the SEM graft in the skull base or the SEM in an endogenous sinus tissue proximal to the SEM graft in the skull base (described herein)) can have an area equal to or less than $0.25$ cm$^2$, $0.5$ cm$^2$, $0.75$ cm$^2$, $1$ cm$^2$, $1.5$ cm$^2$, $2.0$ cm$^2$, $2.5$ cm$^2$, $3.0$ cm$^2$, $3.5$ cm$^2$, $4.0$ cm$^2$, $4.5$ cm$^2$, $5.0$ cm$^2$, $5.5$ cm$^2$, $6.0$ cm$^2$, $6.5$ cm$^2$, $7.0$ cm$^2$, $8$ cm$^2$, $10$ cm$^2$, $12$ cm$^2$, $14$ cm$^2$, $16$ cm$^2$, $18$ cm$^2$, $20$ cm$^2$, $22$ cm$^2$, $24$ cm$^2$, or $25$ cm$^2$.

Formation of an Endonasal Reservoir

Also provided herein are methods for forming an endonasal reservoir in a subject. These methods include forming a SEM graft in the skull base of the subject (as described herein), introducing a SEM graft over an endogenous sinus tissue or at a position proximal to the SEM graft in the skull base of the subject, where the introduction of the SEM graft in the endogenous sinus tissue generates an endonasal reservoir. An endonasal reservoir is defined, in part, by at least two structures or surfaces: (i) a SEM graft in the skull base (as described herein), and (ii) a SEM graft over an endogenous sinus tissue or in a position proximal to the SEM graft in the skull base. In some embodiments, the space between or bordered by the SEM graft in the endogenous sinus tissue and the SEM graft in the skull base includes a pre-existing sinus lumen.

One or more pharmaceutical agents or compositions can be administered into an endonasal reservoir in a subject. The formed endonasal reservoir is proximal to the SEM graft in the skull base and allows for diffusion of at least one pharmaceutical agent from the endonasal reservoir through direct contact with the SEM graft in the skull base into the CNS. In some embodiments, the endonasal reservoir can also contain an access port that allows for repeated (e.g., more than one) administration of at least one pharmaceutical agent or composition into the endonasal reservoir and/or a route of egress for the degradation products of the at least one pharmaceutical agent or composition administered. In some embodiments, the SEM graft in the skull base and the endonasal reservoir are formed in a region of the skull base that allows for unimpeded bilateral diffusion of at least one pharmaceutical agent or composition, while introducing the at least one pharmaceutical agent or composition at a point in the ascending CSF flow cycle (e.g., at a point where the CSF begins to bathe the brainstem, the midbrain, and the bilateral cerebral cortices) (FIG. 2; large black arrow).

In some embodiments, the SEM graft in the skull base and the SEM graft in the endogenous sinus tissue surface can be from the same tissue source (e.g., the endonasal mucosa of the subject). In some embodiments, the SEM graft in the skull base and the SEM graft in the endogenous sinus tissue surface can be from different tissue sources (e.g., the endonasal mucosa and mucosa from the middle turbinate). The surface area of the SEM graft in the skull base and the SEM graft in the endogenous sinus tissue surface can have approximately the same area or can have different areas (e.g., the surface area of the SEM graft in the skull base has a smaller surface area than the SEM graft in the endogenous sinus tissue surface). In some embodiments of all of the methods described herein, the SEM graft in the endogenous sinus tissue can be introduced prior to forming a SEM graft in the skull base of the subject (e.g., at a position that is proximal to the SEM graft in the endogenous sinus tissue surface).

Figure 6:
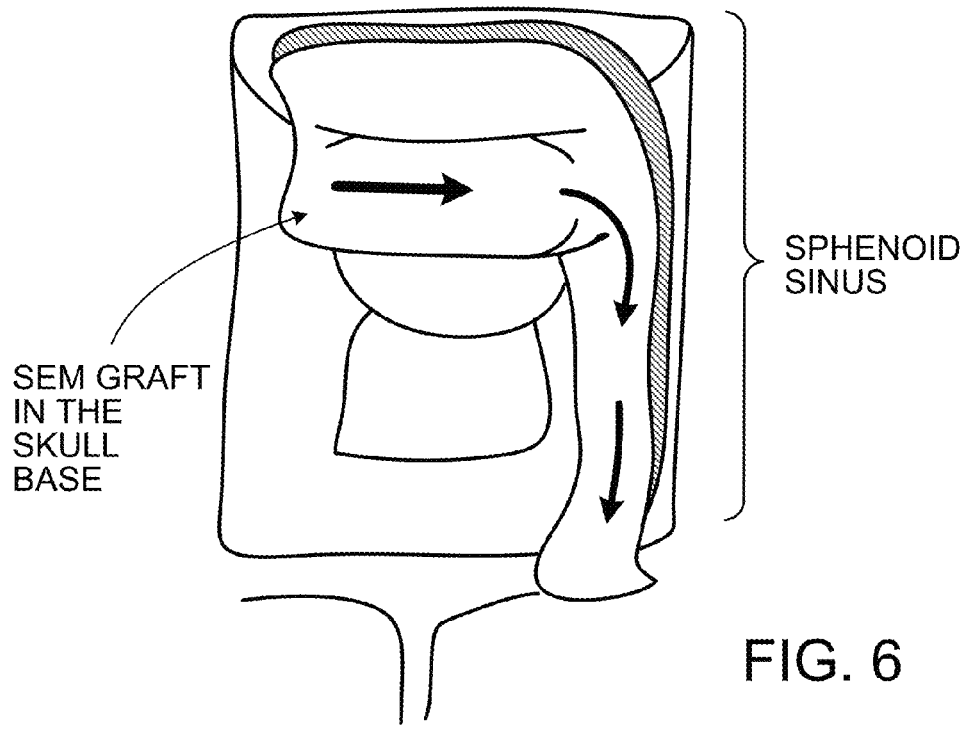
FIG. 6 is a diagram showing the placement of one SEM graft in the skull base. The arrows represent the circulation of substance(s) that occurs within the endogenous sinus tissue of the subject as a result of the ciliary motion of the SEM graft in the skull base.
Figure 7:
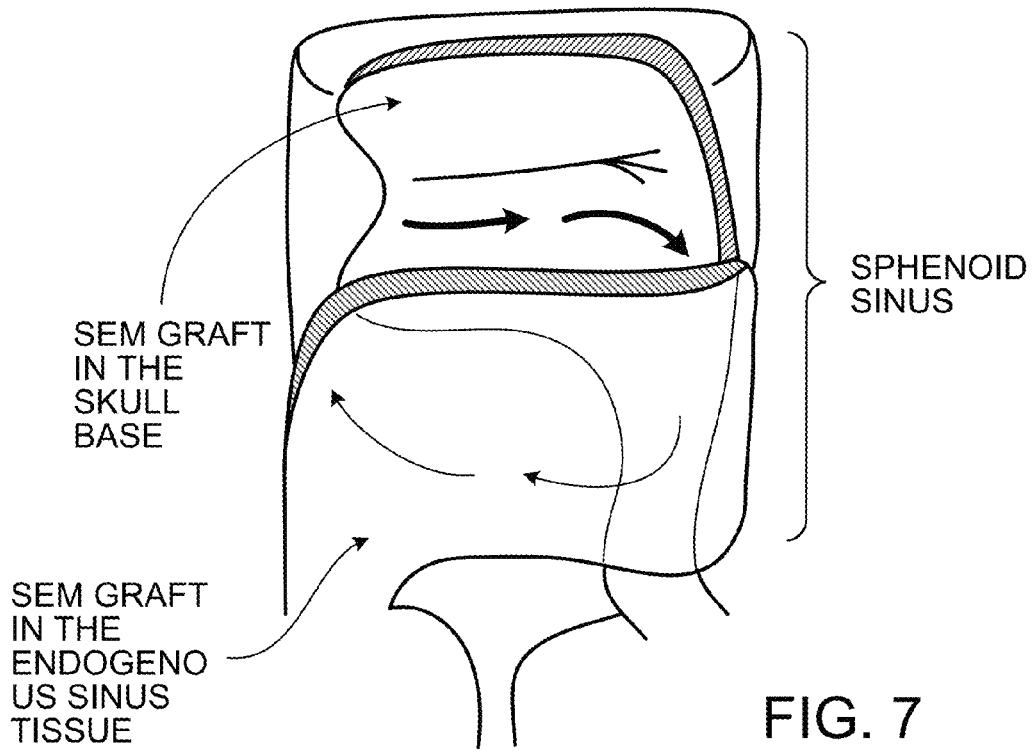
FIG. 7 is a diagram showing the placement of a SEM graft in the skull base and a SEM graft over the face of the sphenoid sinus proximal to the SEM graft in the skull base thereby creating in endonasal reservoir which is partially comprised of the natural sphenoid sinus. The arrows represent the circulation of substance(s) that occurs within the endogenous sinus tissue of the subject as a result of the ciliary motion of the two SEM grafts.

In any of the methods described herein, the SEM graft in the skull base and the SEM in the endogenous sinus tissue surface are positioned such that the cilia present in the SEM graft in the skull base and the SEM graft in the endogenous sinus tissue beat in a lateral to medial direction and are positioned in a manner that allows for an approximately circumferential flow of a liquid pharmaceutical composition (e.g., a liquid containing at least one of any of the pharmaceutical agents described herein) in the endonasal reservoir. FIG. 6 shows the introduction of a SEM graft in the skull base and the flow pattern resulting from the cilia in the SEM graft in the subject's skull base. FIG. 7 shows the introduction of a SEM graft in the skull base (upper section) and a SEM graft in the face of the sphenoid sinus proximal to the SEM graft in the skull base (lower section), and the flow pattern resulting from the cilia in the two SEM grafts.

An endonasal reservoir can contain at least one pharmaceutical agent (e.g., any of the pharmaceutical agents described herein). As described further herein, the at least one pharmaceutical agent can be administered into the endonasal reservoir using a variety of different methods described herein and known in the art. The at least one pharmaceutical agent that is administered into an endonasal reservoir can be formulated in a variety of ways: in a liquid (e.g., a thermosetting liquid), a biodegradable biocompatible polymer (e.g., a gel or solid), or a powder.

In some embodiments, the endonasal reservoir can contain a volume of at least one pharmaceutical agent or composition containing at least one pharmaceutical agent equal to or less than 0.25 mL, 0.5 mL, 0.75 mL, 1.0 mL, 1.5 mL, 2.0 mL, 2.5 mL, 3.0 mL, 3.5 mL, 4.0 mL, 4.5 mL, 5.0 mL, 5.5 mL, 6.0 mL, 6.5 mL, 7.0 mL, 7.5 mL, and 8.0 mL. In some embodiments, the endonasal reservoir has a tissue site or outlet (e.g., an opening or shunt) that allows for the direct administration (e.g., endoscopic administration or injection) of one or more doses of a composition containing at least one pharmaceutical agent (e.g., a liquid, gel, or solid) or allows for the removal of the degradation products of a composition containing at least one pharmaceutical agent that was previously administered into the endonasal reservoir (e.g., lavage of the endonasal reservoir). In some embodiments, a lavage of the endonasal reservoir in the subject is performed prior to the introduction of the next dose of pharmaceutical composition (e.g., a composition containing at least one pharmaceutical agent) into the endonasal reservoir of a subject. As is known in the art, a lavage may be performed using any suitable biological buffer (e.g., saline solution).

In some embodiments, more than one endonasal reservoir may be formed in a subject. For example, an endonasal reservoir can be formed in sinus tissue on both sides of the face.

Endonasal Reservoir Devices

Also provided herein are endonasal reservoir devices and methods of introducing endonasal reservoir devices in a subject. An endonasal reservoir device can be placed into an endogenous sinus tissue of a subject having an SEM graft in their skull base. In some embodiments, an SEM graft is formed in the skull base following the implantation of an endonasal reservoir device in an endogenous sinus tissue of the subject. The combination of a SEM graft in the skull base and the implantation of an endonasal reservoir device in an endogenous sinus tissue in the subject allows for the administration of at least one pharmaceutical agent from the endonasal reservoir device onto the SEM graft in the skull base. Such administration results in the delivery of the pharmaceutical agent(s) in the endonasal reservoir device to the central nervous system of the subject (e.g., the brain).

An endonasal reservoir device is a three-dimensional biocompatible synthetic construct that has a section of tubing (e.g., catheter tubing with an inner diameter of between 0.2 mm to 5 mm) that is connected to a body that has the capacity to contain a volume of a (e.g., at least one) pharmaceutical composition (e.g., any of the pharmaceutical compositions described herein), where the expandable body has an (e.g., at least one) opening (e.g., an opening with a diameter equal to or less than 1.0 cm$^2$) or a permeable surface (e.g., a surface equal to or less than 3.0 cm$^2$) through which the pharmaceutical composition can be administered onto a SEM graft in the skull base of a subject.

The tubing of the device should have a length sufficient to connect the body (placed in an endogenous sinus tissue of a subject) to the sphenoid sinus in the subject. In some embodiments, the tubing of the device has a length between about 1.0 cm and about 15 cm, about 1.0 cm to about 10 cm, about 1.0 cm and about 8.0 cm, about 2.0 cm and about 7.0 cm, about 5.0 cm and about 10 cm, about 1.0 cm and about 4.0 cm, about 4.0 cm and about 8.0 cm, and about 10 cm to about 15 cm). The end of the tubing that is not connected to the body of the device can be closed with a resealable material (e.g., a polymer or material containing silicon) that can be repeatedly punctured by a needle. Upon placement of the device a subject, the end of the tubing that is not connected to the body can be located in the sphenoid sinus such that a needle introduced through the subject's nasal cavity (nostril) can be used to inject at least one pharmaceutical agent into the tubing of the device and thus, fill the body of the device (located in an endogenous sinus tissue) with the at least one pharmaceutical agent. Additional details of filling the device with at least one pharmaceutical agent (e.g., dosing) are described below.

In different embodiments, the at least one opening or permeable surface is circular, ellipsoidal, rectangular, semicircular, square, triangular, pentagonal, or hexagonal. In some embodiments, the permeable surface can be composed of a polymeric permeable mesh or a permeable membrane (e.g., a permeable membrane filter). In some embodiments, the at least one opening has a size equal to or less than 1.5 cm$^2$, 1.4 cm$^2$, 1.2 cm$^2$, 1.0 cm$^2$, 0.8 cm$^2$, 0.6 cm$^2$, 0.4 cm$^2$, 0.3 cm$^2$, 0.2 cm$^2$, or 0.1 cm$^2$. In some embodiments, the at least one permeable surface has an area equal to or less than 3.0 cm$^2$, 2.8 cm$^2$, 2.6 cm$^2$, 2.4 cm$^2$, 2.2 cm$^2$, 2.0 cm$^2$, 1.8 cm$^2$, 1.6 cm$^2$, 1.4 cm$^2$, 1.2 cm$^2$, 1.0 cm$^2$, 0.8 cm$^2$, or 0.5 cm$^2$. The body of the device is placed in the endogenous sinus tissue of the subject such that the at least one opening or permeable surface of the body is proximal to the SEM graft in the subject's skull base.

In some embodiments, the body can be made of an expandable material (e.g., a material containing silicone), such that introduction of at least one pharmaceutical composition into the body of the device results in an increase in the volume of the body of the device. In some embodiments, the body or the tubing of the device can contain, at least in part, silicone, polyethylene, and/or polyetheretherketone. The body of the device is dimensioned such that it fits comfortably within the endonasal sinus tissue of a subject (e.g., when empty or when filled with a volume of a pharmaceutical composition). In embodiments where the body is made of an expandable material, the body is designed such that the fully-expanded body (i.e., the body filled to capacity with the pharmaceutical composition) fits comfortably in the endogenous sinus tissue of a subject. The body of the device can have a variety of different shapes (e.g., conical frustrum-shaped, spherical, rectangular, tubular, or ellipsoidal). The body of the device can contain a volume of a pharmaceutical agent (e.g., equal to or less than 8.0 mL, 7.5 mL, 7.0 mL, 6.5 mL, 6.0 mL, 5.5 mL, 5.0 mL, 4.5 mL, 4.0 mL, 3.5 mL, 3.0 mL, 2.5 mL, 2.0 mL, 1.5 mL, or 1.0 mL).

In some embodiments, the endonasal reservoir devices do not contain tubing and contain an expandable body that contains at least one opening or permeable membrane (e.g., having any of the features described above). In these embodiments, the body is made of resealable material that can be repeatedly injected using a syringe (e.g., through an interfacial procedure). The redosing of these devices can be performed by injecting at least one pharmaceutical composition into the lumen (interior) of the device in the endogenous sinus tissue of the subject.

Figure 8:
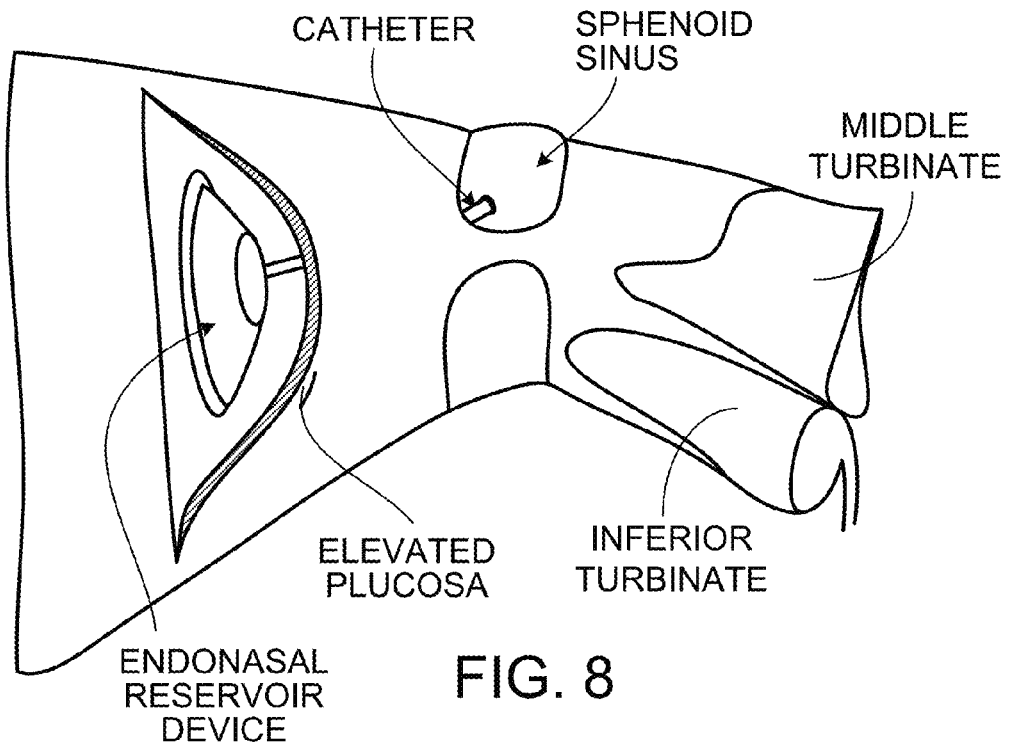
FIG. 8 is a diagram showing the placement of an endonasal reservoir device in an endogenous sinus tissue of the subject. In this diagram, the body of the device has a conical frustrum-shape. The diagram shows the extension of the tubing of the device extending from the body into the sphenoid sinus.
Figure 9:
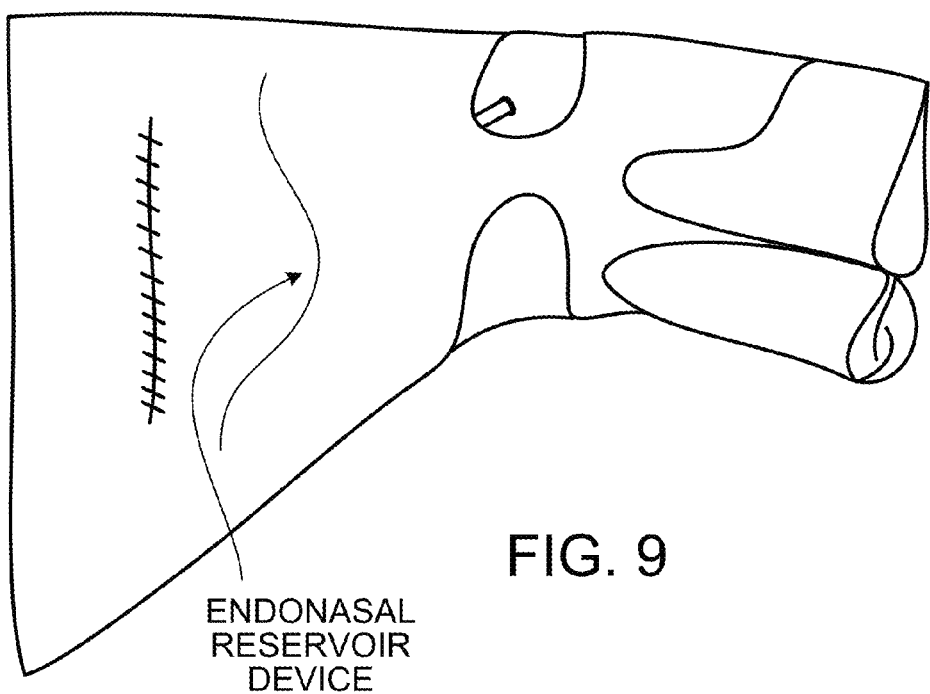
FIG. 9 shows the suturing of the nasal tissue following placement of an endonasal reservoir device into the endogenous sinus tissue of the subject sealing it into a submucosal plane.

FIG. 8 shows the placement of an exemplary endonasal reservoir device in an endogenous sinus tissue of a subject with the tubing of the device extending from the body into the sphenoid sinus. FIG. 9 shows the suturing of the nasal tissue following placement of an endonasal reservoir device into the endogenous sinus tissue of the subject, thereby sealing it into the submucosal plane.

Methods of Delivering Pharmaceutical Agents

Provided herein are methods of administering at least one pharmaceutical agent or composition (e.g., any of the pharmaceutical agents or compositions described herein) to the CNS of a subject. These methods include directly administering at least one pharmaceutical agent or composition containing at least one pharmaceutical agent onto a SEM graft in the skull base of the subject. In some embodiments, the at least one pharmaceutical agent or composition is administered into an endonasal reservoir. In some embodiments, the pharmaceutical agent or composition is administered into an endonasal reservoir device in an endogenous sinus tissue of the subject that is positioned such that the at least one opening or permeable surface of the body is proximal to the SEM graft in the subject's skull base. In some embodiments, the administering results in the delivery of at least one pharmaceutical agent to the brain of the subject.

In some embodiments, the at least one pharmaceutical agent or composition can be administered through an endoscopic procedure (e.g., by directing an endoscopic instrument through the nasal canal of the subject). In some embodiments, the at least one pharmaceutical agent or composition is administered by endoscopically guiding a tube through the nasal canal of the subject into the endonasal reservoir or to the SEM graft in the skull base, such that a volume of a liquid, gel, or solid pharmaceutical composition containing at least one pharmaceutical agent can be administered through the tube into the endonasal reservoir or onto the SEM graft in the skull base. In some embodiments, the at least one pharmaceutical agent or composition can be introduced into an endonasal reservoir device (e.g., injected into the end of the tubing located in the sphenoid sinus of a subject or injected directly into the lumen of the body of the device) through an endoscopic procedure or through use of a nasal speculum. In some embodiments, the injection of the at least one pharmaceutical agent or composition into the tubing of the device pushes the agent/composition (via hydrodynamic force) into the body of the device. The filled body of the device then releases the agent/composition through the at least one opening or permeable surface onto the proximally located SEM graft in the skull base of the subject.

In some embodiments, the at least one pharmaceutical agent or composition can be administered into the endonasal reservoir, the endonasal reservoir device, or onto the SEM graft in the skull base by injection through the facial tissue of the subject. In some embodiments, the injection can be performed using a cannula and an imaging device (e.g., MRI or ultrasound) that images the position of the tip of the cannula relative to the SEM graft in the skull base, the endonasal reservoir, or the endonasal reservoir device. In the embodiments that utilize injection through the facial tissue, the cannula should not pierce the SEM graft in the skull base.

At least one dose (e.g., at least 2, 3, 4, 5, 10, 20, 40, or 60 doses) of a composition containing at least one pharmaceutical agent can be administered to the subject over time. The subject can be administered multiple doses (e.g., two or more doses) of a composition containing at least one pharmaceutical agent over an extended or chronic treatment period (e.g., for at least 1 week, 2 weeks, 1 month, 2 months, 6 months, 1 year, 2 years, 3 years, 4 years, 5 years, 6 years, 7 years, 8 years, 9 years, 10 years, 15 years, 20 years, 25 years, or 30 years). The dosage of the at least one pharmaceutical agent can be adjusted by a health care professional (e.g., a physician) based on a number of factors including: the particular pharmaceutical agent(s) administered, the physical condition of the subject (e.g., weight and the identity and number of disorders), and the subject's sex, weight, and age.

Two or more doses of a composition containing at least one pharmaceutical agent can be administered at any frequency of at least once a week, once every 2 weeks, once every 3 weeks, once a month, once every 2 months, once every 3 months, once every 4 months, once every 5 months, or once every 6 months. The frequency of the administration of two or more doses of a composition containing at least one pharmaceutical agent will depend on the half-life of the composition in vivo. For example, the administration of an additional or the next dose of a pharmaceutical composition containing at least one pharmaceutical agent can be performed once the immediately prior dose of the composition has fully degraded, partially degraded, and/or there is a sub-therapeutic amount of the at least one pharmaceutical agent remaining in the subject. In some embodiments, the two of more doses of a pharmaceutical composition (e.g., any of the pharmaceutical compositions described herein) are administered at a frequency that decreases or prevents any significant fluctuations in the dosage of the at least one pharmaceutical agent delivered to the CNS of the subject. As described herein, in some embodiments a (e.g., one or more) lavage can be performed to remove the degradation products of a previously administered dosage of a pharmaceutical composition (e.g., a composition containing at least one pharmaceutical agent) prior to the administration of the next dosage of the composition. For example, a lavage may be performed to remove degradation products from the endonasal reservoir or the endonasal reservoir device prior to administration of the next dosage of the composition. The number, identity, and/or dosage of pharmaceutical agents delivered to the subject can be varied during treatment (as described further herein).

The methods provided herein allow for the targeted administration of at least one pharmaceutical agent to the CNS of the subject, and therefore can decrease the toxicity or adverse side effects of at least one pharmaceutical agent (e.g., a neuromodulatory or chemotherapeutic agent) in non-targeted tissues (e.g., tissues outside of the CNS). In view of the targeted administration provided by the methods described herein, a dosage of at least one pharmaceutical agent that induces adverse side effects or toxicity when systemically administered to the subject can be administered to subject's CNS system without inducing toxicity or adverse side effects.

The pharmaceutical agent(s) or composition(s) (e.g., any of pharmaceutical compositions or agents described herein) can be administered to any subject (e.g., a female, a male, a child, an adult, a subject greater than 50 years old, a subject greater than 60 years old, a subject greater than 70 years old, a subject greater than 80 years old). A subject administered the at least one pharmaceutical agent or composition containing at least one pharmaceutical agent can be previously diagnosed as having a neurological disorder (e.g., any of the neurological disorders described herein) or identified as being in pain (e.g., having chronic pain). In some embodiments, a subject can be administered at least one pharmaceutical agent or composition containing at least one pharmaceutical agent within 1 week, 2 weeks, 3 weeks, or 1 month of the formation of a SEM graft in the skull base or an endonasal reservoir, or the formation of a SEM graft in the skull base and the placement of the endonasal reservoir device in an endogenous sinus tissue in the subject (e.g., using any of the methods described herein).

The at least one pharmaceutical agent or composition containing at least one pharmaceutical agent can be administered by a health care professional (e.g., a nurse, physician's assistant, a laboratory technician, or a physician). The administration of at least one pharmaceutical agent or composition containing at least one pharmaceutical agent can be performed in a clinic (e.g., health care clinic) or out-patient facility, a hospital, or in an assisted-living facility (e.g., hospice care center or nursing home).

Pharmaceutical Compositions

Also provided are pharmaceutical compositions containing at least one pharmaceutical agent for use in any of the methods described herein. The pharmaceutical compositions can be delivered to the CNS of the subject using any of the methods described herein. In non-limiting embodiments, the compositions contain at least one pharmaceutical agent with a molecular size of greater than 500 Da (e.g., greater than 600 Da, 700 Da, 800 Da, 900 Da, 1 kDa, 2 kDa, 3 kDa, 4 kDa, 5 kDa, 10 kDa, 20 kDa, 30 kDa, 70 kD, or 100 kD) or a net positive or net negative charge. In some embodiments, the compositions contain at least one pharmaceutical agent that is a polar molecule.

In some embodiments, the at least one pharmaceutical agent present in the composition decreases unregulated or mis-regulated cell growth (e.g., reduces the rate of cancer cell growth), mediates or induces cancer cell death (e.g., necrosis or apoptosis), decreases protein misfolding and/or aggregation, mediates an increase or decrease in neurohormone or neurotransmitter production or turn-over, decreases loss of myelin, reduces neuronal cell death or neuronal loss, reduces loss of axons, mediates an increase or decrease in neurohormone or neurotransmitter receptor activity, mediates an increase or decrease in synaptic transmission between neurons, and mediates an increase or decrease in neuronal intracellular signaling pathways. In some compositions, the at least pharmaceutical agent is an analgesic.

In some embodiments, the delivery of a composition containing at least one pharmaceutical agent results in a decrease (e.g., a significant, detectable, or observable decrease) in the number of symptoms or the number, frequency, or duration of one or more symptoms of disease (e.g., a neurological disorder) in a subject. In some non-limiting embodiments, the at least one pharmaceutical agent present in the composition can be a chemotherapeutic agent, L-DOPA, carbidopa, an anti-depressant agent, an anti-psychotic agent, donepezil, rivastigmine tartrate, galantamine, memantine, ISIS-SOD1, ISIS-SMN, ISIS-TTR, ELND005, β- or γ-secretase inhibitors, neurotrophic peptides, nanoparticles, fusion proteins, and gene therapy vectors. Additional pharmaceutical agents are known in the art.

Non-limiting examples of chemotherapeutic agents include proteins (e.g., antibodies, antigen-binding fragments of antibodies, or conjugates or derivatives thereof), nucleic acids, lipids, or small molecules, or combinations thereof. Non-limiting examples of chemotherapeutic agents include: cyclophosphamide, mechlorethamine, chlorabucil, melphalan, daunorubicin, doxorubicin, epirubicin, idarubicin, mitoxantrone, valrubicin, paclitaxel, docetaxel, etoposide, teniposide, tafluposide, azacitidine, azathioprine, capecitabine, cytarabine, doxifluridine, fluorouracil, gemcitabine, mercaptopurine, methotrexate, tioguanine, bleomycin, carboplatin, cisplatin, oxaliplatin, all-trans retinoic acid, vinblastine, vincristine, vindesine, vinorelbine, and bevacizumab (or an antigen-binding fragment thereof). Additional examples of chemotherapeutic agents are known in the art.

Non-limiting examples of anti-depressant agents include: selective serotonin reuptake inhibitors (e.g., citalopram, escitalopram, fluoxetine, paroxetine, or sertraline), serotonin-norepinephrine reuptake inhibitors (e.g., desvenlafaxine, duloxetine, milnacipran, and venlafaxine), noradrenergic and specific serotonergic antidepressants (e.g., mianserin and mirtazapine), norephinephrine reuptake inhibitors (e.g., atomoxetine, mazindol, reboxetine, and viloxazine), norepinephrine-dopamine reuptake inhibitors (e.g., bupropion), selective serotonin reuptake enhancers (e.g., tianeptine), norephinephrine-dopamine disinhibitors (e.g., agomelatine), tricyclic antidepressants (e.g., amitriptyline, clomipramine, doxepin, imipramine, and trimipramine), secondary amine tricyclic depressants (e.g., desipramine, nortriptyline, and protripyline), monoamine oxidase inhibitors (e.g., isocarboxazid, moclobemide, phenelzine, selegiline, and tranylcypromine), buspirone, gepirone, nefazodone, trandospirone, trazodone, bupropion, benzodiazepines, amphetamine, methylphenidate, modafinil, lithium, carbamazepine, sodium valproate, and lamotrigine. Non-limiting examples of anti-psychotic agents include risperidone, olanzapine, and quetiapine. Additional examples of anti-depressant and anti-psychotic agents are known in the art.

At least one composition containing at least one pharmaceutical agent can be formulated using any methods known in the art. In non-limiting examples, the composition containing at least one pharmaceutical agent is formulated as a liquid (e.g., a thermosetting liquid), as a component of a solid (e.g., a powder or a biodegradable biocompatible polymer (e.g., a cationic biodegradable biocompatible polymer)), or as a component of a gel (e.g., a biodegradable biocompatible polymer). In some embodiments, the at least composition containing at least one pharmaceutical agent is formulated as a gel selected from the group of an alginate gel (e.g., sodium alginate), a cellulose-based gel (e.g., carboxymethyl cellulose or carboxyethyl cellulose), or a chitosan-based gel (e.g., chitosan glycerophosphate). Additional, non-limiting examples of drug-eluting polymers that can be used to formulate any of the pharmaceutical compositions described herein include, carrageenan, carboxymethylcellulose, hydroxypropylcellulose, dextran in combination with polyvinyl alcohol, dextran in combination with polyacrylic acid, polygalacturonic acid, galacturonic polysaccharide, polysalactic acid, polyglycolic acid, tamarind gum, xanthum gum, cellulose gum, guar gum (carboxymethyl guar), pectin, polyacrylic acid, polymethacrylic acid, N-isopropylpolyacrylomide, polyoxyethylene, polyoxypropylene, pluronic acid, polylactic acid, cyclodextrin, cycloamylose, resilin, polybutadiene, N-(2-Hydroxypropyl)methacrylamide (HPMA) copolymer, maleic anhydrate-alkyl vinyl ether, polydepsipeptide, polyhydroxybutyrate, polycaprolactone, polydioxanone, polyethylene glycol, polyorganophosphazene, polyortho ester, polyvinylpyrrolidone, polylactic-co-glycolic acid (PLGA), polyanhydrides, polysilamine, poly N-vinyl caprolactam, and gellan.

The compositions described herein are not limited to the exemplary pharmaceutical agents described herein. Any pharmaceutical agent that demonstrates increased permeability in the SEM graft in the skull base compared to the permeability of the same molecule in the BBB can be included in the compositions described herein and may delivered to the CNS using any of the methods described herein. The pharmaceutical agents that can be included in the compositions described herein are not limited by their biophysical or electrochemical features or by the composition of the pharmaceutical agent.

In some embodiments, the at least one pharmaceutical agent is formulated in a composition that continuously releases the at least one pharmaceutical agent onto the SEM graft in the skull base (e.g., avoids an initial spike in the release of the at least one pharmaceutical agent onto the SEM graft in the skull base). In some embodiments, the composition containing the at least one pharmaceutical agent is a sustained-release composition (e.g., allows for the release of the at least one pharmaceutical agent over a period of time). In some embodiments, the at least one pharmaceutical agent is formulated in a composition (e.g., a sustained-release formulation) that releases the at least one pharmaceutical agent onto the SEM graft in the skull base over a period of at least 3 days, 1 week, 2 weeks, 3 weeks, 1 month, 2 months, or 3 months. In some embodiments, the at least one pharmaceutical agent has an in vivo half-life (e.g., the amount of time between the administration of the at least one pharmaceutical agent and the point in time where 50% of the biological activity of the at least one pharmaceutical agent is present in the subject) of at least 1 week, 2 weeks, 3 weeks, 1 month, 5 weeks, 6 weeks, 7 weeks, 2 months, 9 weeks, 10 weeks, 11 weeks, or 3 months.

The at least one pharmaceutical agent can be formulated with one or more permeation enhancers (e.g., surfactants, bile salts, lipids, cyclodextrins, polymers, and tight junction modifiers) in order to increase the passage of the pharmaceutical agent(s) across the SEM graft in the skull base into the subarachnoid space. In some embodiments, the pharmaceutical agent(s) are formulated with laurocarnitine. The pharmaceutical agent(s) can also be formulated using different osmolarities. For example, pharmaceutical agent(s) can be formulated in an isotonic solution in order to increase the passage of the pharmaceutical agent(s) across the SEM graft in the skull base into the subarachnoid space. In some embodiments, the pharmaceutical agent(s) are formulated in acidic or basic solutions (e.g., formulated such that the pharmaceutical agent(s) are unionized or the fraction of ionized pharmaceutical agent present in the composition is reduced). In some embodiments, the pharmaceutical agent(s) are formulated in acidic or basic solution such that the pharmaceutical agent(s) present in the composition have a net negative charge.

In some embodiments, the pharmaceutical agent(s) can be formulated with one or more of: a mucoadhesive agent(s), surface-engineered nanoparticles, efflux transporter inhibitors, and vasoconstrictors. The addition of these secondary agents to the formulations can reduce mucociliary clearance, prolong the residence time of the pharmaceutical agent(s) at the delivery site, and increase transport across the SEM graft in the skull base. For example, formulations including mucoadhesives, such as acrylic acid derivatives, lectin, and low methylated pectin, form a viscous gel upon contact with a SEM, resulting in reduced clearance from the site of administration. Chitosan, a cationic mucoadhesive, forms electrostatic interactions with the negatively-charged surface of epithelial cells to reduce clearance from the nasal epithelium. Chitosan has the additional effect of reversibly opening tight junctions, which increases the rate of transport across the SEM graft in the skull base. In some embodiments, the pharmaceutical agent(s) are formulated as a micro-emulsion formulation containing a mucoadhesive. In some embodiments, the pharmaceutical compositions contain the pharmaceutical agent(s) and an emulsifying agent (e.g., castor oil, Cremophor RH40).

In some embodiments, the pharmaceutical agent(s) are formulated as surface-engineered nanoparticles with ligands that bind to cellular structures present in an SEM. For example, the engineered nanoparticles can contain the ligand ulex europeus agglutinin I and/or wheat germ agglutinin. In some embodiments, the compositions can further contain an inhibitor of P-gp efflux transport protein (e.g., rifampin). In some embodiments, the compositions can further contain a vasoconstrictor (e.g., phenylephrine).

The amount of the at least one pharmaceutical agent that can be present in a single dose of a pharmaceutical composition can be between 1 mg and 800 mg, between 1 mg and 20 mg, between 20 mg and 50 mg, between 50 mg to 100 mg, between 100 mg and 200 mg, between 200 mg and 300 mg, between 300 mg and 400 mg, between 400 mg and 500 mg, between 500 mg and 600 mg, between 600 mg and 700 mg, between 700 mg and 800 mg, between 50 mg and 500 mg, between 200 mg and 600 mg, and between 400 mg and 800 mg. The volume of a dose of a composition (e.g., a solid, liquid, or gel) containing at least one pharmaceutical agent can between 0.1 mL to 10 mL, between 0.1 mL to 1 mL, between 1 mL to 2 mL, between 2 mL to 3 mL, between 3 mL to 4 mL, between 4 mL to 5 mL, between 5 mL to 6 mL, between 6 mL to 7 mL, between 7 mL to 8 mL, between 1 mL and 5 mL, between 5 mL and 10 mL, and between 3 mL and 8 mL. As described further herein, the volume or dosage of a composition containing at least one pharmaceutical agent can be adjusted by a health care professional during the treatment of a subject. In some embodiments, a health care professional may also add and/or remove one of more pharmaceutical agents from the administered composition during treatment.

In some embodiments, the at least one pharmaceutical agent is formulated in a composition that breaks down into decomposition products that are naturally cleared from the endonasal tissue or the endonasal reservoir (e.g., the degradation products are soluble in sinus fluid or mucus and are cleared by mucociliary clearance from the sinonasal passages). In some embodiments, the at least one pharmaceutical agent is formulated in a pharmaceutical composition that breaks down into decomposition products that do not stimulate an inflammatory response or an immune response in the subject. In some embodiments, the at least one pharmaceutical agent is formulated in a pharmaceutical composition that does not break down into decomposition products that significantly block or obstruct the sinonasal passages of the subject. The ability of a pharmaceutical composition to block or obstruct the sinonasal passages can be determined by endoscopic visualization of the subject's sinonasal tissues. The ability of a pharmaceutical composition to block or obstruct the sinonasal passage can also be determined by detecting or observing one or more symptoms of sinonasal passage blockage or obstruction in the subject (e.g., headache or sinus pressure or discomfort). An inflammatory or an immune response in a subject's sinonasal passages can be determined using methods known in the art including: observation or detection of at least one symptom of sinitis (e.g., drainage of a thick, yellow or greenish discharge from the nose or down the back of the throat, nasal obstruction or congestion, difficulty breathing through the nose, pain, tenderness, swelling, or pressure around the eyes, cheeks, nose, or forehead, pain in the upper jaw or teeth, reduced sense of smell and taste, cough, ear pain, headache, sore throat, halitosis, fatigue, and fever). An inflammatory or an immune response in a subject may also be determined using one or more diagnostic tests known in the art (e.g., enzyme-linked immunosorbence assay (ELISA) for elevated levels of C-reactive protein, interleukin-1β, interleukin-6, interleukin-8, interleukin-10, and TNF-α).

Any of the pharmaceutical compositions containing at least one of any of the pharmaceutical agents described herein can be packaged with one or more additional instruments for delivering the composition onto the SEM graft in the skull base, into the endonasal reservoir, or into the endonasal reservoir device. Any of the pharmaceutical compositions containing at least one of any of the pharmaceutical agents described herein can also be packaged with instructions for administering the composition onto the SEM graft in the skull base, into the endonasal reservoir, or into the endonasal reservoir device in the subject. For example, the pharmaceutical compositions may be packed with instructions that specify that the pharmaceutical composition be administered to a subject having an SEM graft in their skull base, an endonasal reservoir, or an endonasal reservoir device (e.g., an SEM graft, an endonasal reservoir, or an endonasal reservoir device formed or implanted using any of the methods described herein).

Methods for Treating Neurological Disorders and Pain

Also provided herein are methods of treating a neurological disorder or pain (e.g., chronic pain) in a subject that has a SEM graft in their skull base that include directly administering at least one pharmaceutical agent (or at least one composition that contains at least one pharmaceutical agent) onto the SEM graft in the skull base of the subject or into an endonasal reservoir in the subject. Also provided herein are methods of treating a neurological disorder or pain in a subject that has both a SEM graft in their skull base and an endonasal reservoir device (as described herein).

Also provided are methods of treating a neurological disorder or pain in a subject that include forming a SEM graft in the skull base of the subject and administering at least one pharmaceutical agent onto the SEM graft in the skull base in the subject. Some embodiments of the methods further include introducing a SEM graft over an endogenous sinus tissue or at a position proximal (e.g., roughly parallel) to the SEM graft in the skull base, where the SEM graft in the endogenous sinus tissue forms an endonasal reservoir. The SEM graft in the endogenous sinus tissue may be introduced either before or after forming the SEM graft in the skull base of the subject. Some embodiments of the methods further include introducing an endonasal reservoir device in an endogenous sinus tissue and forming an SEM graft in the skull base. In these embodiments, the SEM graft in the skull base can be formed in the skull base of the subject prior to the introduction of the endonasal reservoir device in the endogenous sinus tissue, or the endonasal reservoir device can be introduced into an endogenous sinus tissue prior to the formation of the SEM graft in the skull base of the subject. In these embodiments, the at least one pharmaceutical agent or composition is placed in the device and the agent/composition is released from the at least one opening or permeable surface of the device's body onto the SEM graft in the skull base of the subject.

In some embodiments of these methods, the forming of SEM graft in the skull base, the forming of a SEM graft in an endogenous sinus tissue surface of the subject, the introducing of an endonasal reservoir device, the administering of the agent/composition onto the SEM graft in the skull base, the administering of the agent/composition into the endonasal reservoir, and/or the placing/introducing of the agent/composition into the endonasal reservoir device is performed, e.g., by an endoscopic procedure (e.g., through the nasal canal of the subject), an interfacial procedure (e.g., injection or surgery), or an intracranial procedure (e.g., injection or surgery). In some embodiments of any of the methods described herein, the at least one pharmaceutical agent or at least one composition containing the at least one pharmaceutical agent is administered into an endonasal reservoir or placed into an endonasal reservoir device. In some embodiments of any of the methods described herein, the at least one pharmaceutical agent is delivered to the brain of the subject.

In some embodiments, the SEM graft in the skull base or the SEM graft in an endogenous sinus tissue is formed from sinonasal mucosa (e.g., autologous or heterologous sinonasal mucosa). Any of the SEMs described herein can be used to form the SEM graft in the skull base or the SEM graft in the endogenous sinus tissue surface without limitation.

Any neurological disorder can be treated using any of the methods described herein. A neurological disorder is a disease or condition that affects the central nervous system (e.g., the brain or the spinal cord). Non-limiting examples of neurological disorders have one of more (e.g., two, three, or four) of the following features: unregulated or mis-regulated cell growth (e.g., a brain cancer), a pathological increase in neuronal cell death (e.g., necrosis or apoptosis), a pathological decrease in axon number, pathological protein misfolding and/or aggregation, a pathological loss of myelin, a pathological increase or decrease in neurohormone or neurotransmitter production or turn-over, a pathological increase or decrease in neurohormone or neurotransmitter receptor activity, a pathological increase or decrease in synaptic transmission between neurons, and a pathological increase or decrease in neuronal intracellular signaling pathways. Non-limiting examples of neurological disorders can be manifested or diagnosed by the observation of one or more (e.g., two, three, or four) of the following symptoms: forgetfulness, confusion, difficulty speaking, loss of memory, disorientation, difficulty writing, depression, anxiety, social withdrawal, mood swings, irritability, sleeping problems (e.g., insomnia), wandering, tremor, slowed motion (bradykinesia), rigid muscles, impaired posture or balance, muscle weakness, loss of coordination, headache, seizures, nausea, double vision or blurred vision, lethargy, and overeating or appetite loss. Non-limiting examples of neurological disorders include: Parkinson's disease, Alzheimer's disease, a brain cancer (e.g., glioblastoma multiforme, oligodendroglioma, astrocytoma, oligoastrocytoma, ependymoma, medulloblastoma, or meningioma), Huntington's disease, Bell's palsy, stroke, epilepsy, migraine, a sleep disorder, multiple sclerosis, muscular dystrophy, amyotrophic lateral sclerosis, encephalitis, Creutzfeldt-Jakob disease, meningitis, frontotemporal dementia, schizophrenia, and depression.

Additional non-limiting examples of neurological disorders include: Acid Lipase Disease, Acid Maltase Deficiency, Acquired Epileptiform Aphasia, Acute Disseminated Encephalomyelitis, Attention Deficit Hyperactivity Disorder, Adie's Syndrome, Adrenoleukodystrophy, Agenesis of the Corpus Callosum, Agnosia, Aicardi Syndrome, Aicardi-Goutieres Syndrome Disorder, Neurological Complications of AIDS, Alexander Disease, Alpers' Disease, Alternating Hemiplegia, Anencephaly, Aneurysm, Angelman Syndrome, Angiomatosis, Anoxia, Antiphospholipid Syndrome, Aphasia, Apraxia, Arachnoid Cysts, Arachnoiditis, Asperger Syndrome, Ataxia, Ataxia Telangiectasia, Cerebellar or Spinocerebellar Degeneration, Autism, Barth Syndrome, Batten Disease, Becker's Myotonia, Behcet's Disease, Bell's Palsy, Benign Essential Blepharospasm, Benign Intracranial Hypertension, Bernhardt-Roth Syndrome, Binswanger's Disease, Bloch-Sulzberger Syndrome, Bradbury-Eggleston Syndrome, Spinal Tumors, Brain Injury, Brown-Sequard Syndrome, Bulbospinal Muscular Atrophy, Canavan Disease, Causalgia, Cavernomas, Cavernous Angioma, Central Cervical Cord Syndrome, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysm, Cerebral Arteriosclerosis, Cerebral Atrophy, Cerebral Beriberi, Cerebral Cavernous Malformation, Cerebral Gigantism, Cerebral Hypoxia, Cerebral Palsy, Cerebro-Oculo-Facio-Skeletal Syndrome (COFS), Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, Colpocephaly, Coma, Complex Regional Pain Syndrome, Congenital Facial Diplegia, Corticobasal Degeneration, Cranial Arteritis, Craniosynostosis, Cree encephalitis, Creutzfeldt-Jakob Disease, Cumulative Trauma Disorders, Cushing's Syndrome, Cytomegalic Inclusion Body Disease, Cytomegalovirus Infection, Dandy-Walker Syndrome, Dawson Disease, De Morsier's Syndrome, Dejerine-Klumpke Palsy, Dementia (e.g., multi-infarct, semantic, subcortical, and lewy-body associated dementia), Dentate Cerebellar Ataxia, Dentatorubral Atrophy, Dermatomyositis, Devic's Syndrome, Diffuse Sclerosis, Dravet Syndrome, Dysautonomia, Dysgraphia, Dyslexia, Dysphagia, Dyspraxia, Dyssynergia Cerebellaris Myoclonica, Dyssynergia Cerebellaris Progressiva, Dystonias, Early Infantile Epileptic Encephalopathy, Empty Sella Syndrome, Encephalitis, Encephalitis Lethargica, Encephaloceles, Encephalopathy, Encephalopathy (familial infantile), Encephalotrigeminal Angiomatosis, Epilepsy, Epileptic Hemiplegia, Erb-Duchenne and Dejerine-Klumpke Palsies, Erb's Palsy, Essential Tremor, Extrapontine Myelinolysis, Fabry Disease, Fahr's Syndrome, Familial Dysautonomia, Familial Hemangioma, Familial Idiopathic Basal Ganglia Calcification, Familial Periodic Paralyses, Familial Spastic Paralysis, Farber's Disease, Febrile Seizures, Fibromuscular Dysplasia, Fisher Syndrome, Floppy Infant Syndrome, Friedreich's Ataxia, Frontotemporal Dementia, Gangliosidoses, Gaucher's Disease, Gerstmann's Syndrome, Gerstmann-Straussler-Scheinker Disease, Giant Axonal Neuropathy, Giant Cell Arteritis, Giant Cell Inclusion Disease, Globoid Cell Leukodystrophy, Glossopharyngeal Neuralgia, Guillain-Barré Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hydranencephaly, Hydrocephalus, Normal Pressure Hydrocephalus, Hydromyelia, Hypercortisolism, Hypersomnia, Hypertonia, Hypotonia, Hypoxia, Immune-Mediated Encephalomyelitis, Infantile Hypotonia, Infantile Neuroaxonal Dystrophy, Infantile Phytanic Acid Storage Disease, Infantile Refsum Disease, Infantile Spasms, Iniencephaly, Intracranial Cysts, Intracranial Hypertension, Isaac's Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Klüver-Bucy Syndrome, Korsakoffs Amnesic Syndrome, Krabbe Disease, Kugelberg-Welander Disease, Kuru, Lambert-Eaton Myasthenic Syndrome, Landau-Kleffner Syndrome, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lissencephaly, Locked-In Syndrome, Lou Gehrig's Disease, Neurological Sequelae of Lupus, Neurological Complications of Lyme Disease, Machado-Joseph Disease, Macrencephaly, Megalencephaly, Melkersson-Rosenthal Syndrome, Meningitis, Menkes Disease, Meralgia Paresthetica, Metachromatic Leukodystrophy, Microcephaly, Migraine, Miller Fisher Syndrome, Mini Stroke, Moebius Syndrome, Motor Neuron Diseases, Moyamoya Disease, Mucolipidoses, Mucopolysaccharidoses, Multifocal Motor Neuropathy, Multi-Infarct Dementia, Multiple Sclerosis, Multiple System Atrophy with Orthostatic Hypotension, Muscular Dystrophy, Myasthenia Gravis, Myelinoclastic Diffuse Sclerosis, Myoclonic Encephalopathy, Myoclonus, Narcolepsy, Neuroacanthocytosis, Neurodegeneration with Brain Iron Accumulation, Neurofibromatosis, Neuroleptic Malignant Syndrome, Neurological Consequences of Cytomegalovirus Infection, Neurological Manifestations of Pompe Disease, Neuromyotonia, Neuronal Ceroid Lipofuscinosis, Neuronal Migration Disorders, Hereditary Neuropathy, Neurosarcoidosis, Neurosyphilis, Neurotoxicity, Nevus Cavernosus, Niemann-Pick Disease, Normal Pressure Hydrocephalus, Occipital Neuralgia, Ohtahara Syndrome, Olivopontocerebellar Atrophy, Opsoclonus Myoclonus, Orthostatic Hypotension, O'Sullivan-McLeod Syndrome, Overuse Syndrome, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Phytanic Acid Storage Disease, Pick's Disease, Pinched Nerve, Piriformis Syndrome, Pituitary Tumors, Polymyositis, Pompe Disease, Porencephaly, Postherpetic Neuralgia, Postinfectious Encephalomyelitis, Post-Polio Syndrome, Primary Lateral Sclerosis, Primary Progressive Aphasia, Prion Diseases, Progressive Locomotor Ataxia, Progressive Multifocal Leukoencephalopathy, Progressive Supranuclear Palsy, Prosopagnosia, Pseudo-Torch syndrome, Pseudotoxoplasmosis syndrome, Pseudotumor Cerebri, Ramsay Hunt Syndrome I, Ramsay Hunt Syndrome II, Rasmussen's Encephalitis, Reflex Sympathetic Dystrophy Syndrome, Refsum Disease, Repetitive Motion Disorders, Restless Legs Syndrome, Retrovirus-Associated Myelopathy, Rett Syndrome, Reye's Syndrome, Rheumatic Encephalitis, Riley-Day Syndrome, Saint Vitus Dance, Sandhoff Disease, Schilder's Disease, Schizencephaly, Seitelberger Disease, Seizure Disorder, Semantic Dementia, Septo-Optic Dysplasia, Severe Myoclonic Epilepsy, Shingles, Shy-Drager Syndrome, Sjögren's Syndrome, Sleep Apnea, Sotos Syndrome, Spasticity, Spina Bifida, Spinal Cord Infarction, Spinal Cord Injury, Spinal Cord Tumors, Spinocerebellar Atrophy, Spinocerebellar Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, SUNCT Headache, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Tethered Spinal Cord Syndrome, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vasculitis Syndromes of the Central and Peripheral Nervous Systems, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whipple's Disease, Williams Syndrome, Wilson's Disease, Wolman's Disease, and Zellweger Syndrome. These disorders are well known in the art, and methods of diagnosing them are known. A description and exemplary symptoms of each of the above neurological disorders are described at the National Institute of Neurological Disorders and Stroke website (address: ninds.nih.gov/index.htm). Additional examples of neurological disorders are known in the art. Additional methods for diagnosing a neurological condition are also known in the art and include without limitation: the mini-mental state examination, clinical dementia rating, and Beck Depression Inventory or BDI score.

In some embodiments, the subject has a condition listed in the left column of following table, and the methods include administering one or more agents listed in the right column.

| Neurological Disorder | Pharmaceutical Agent |
|---|---|
| Huntington's Disease | Tetrabenazine, Haloperidol, Clozapine, Clonazepam |
| Multiple Sclerosis | Interferon beta-1a, Interferon beta-1b, Glatiramer acetate, Mitoxantrone, Natalizumab, Brain Derived Neurotrophic Factor |
| Parkinson's Disease | Glial Derived Neurotrophic Factor, Artane, Cogentin, Carbidopa/levodopa, Pramipexole, Ropinirole, Rotigotine, Amantadine, Entacapone Tolcapone, Selegiline, and Rasagaline |
| Alzheimer's Disease | Namenda, Razadyne, Reminyl, Exelon, Aricept, Cognex |

Any type of pain, such as chronic pain (e.g., nociceptive pain or neuropathic pain), malignant pain, breakthrough pain, allodynia, paresthesia, hyperpathia, complex regional pain syndrome I, complex regional pain syndrome II, phantom limb pain, psychogenic pain, anesthesia dolorosa, and idiopathic pain can be treated using the methods described herein. In the methods of treating pain (e.g., all of the embodiments described herein), the at least one pharmaceutical agent administered is an analgesic or the at least one pharmaceutical composition administered contains an analgesic. Non-limiting examples of analgesics are described herein. Additional analgesics are known in the art.

Subjects treated using the methods described herein can have a SEM graft in their skull base, can have both a SEM graft in their skull base and a SEM over an endogenous sinus tissue or in a position proximal to the SEM graft in the skull base (an endonasal reservoir), or can have both a SEM graft in their skull base and an endonasal reservoir device placed in an endogenous sinus tissue, such that the at least one opening or permeable surface of the device's body is located proximal to the SEM graft in the skull base of the subject. In some embodiments, the SEM graft in the skull base, the SEM over an endogenous sinus tissue or in a position proximal to the SEM graft in the skull base, and the endonasal reservoir device are formed/introduced using any of the methods described herein. In some embodiments, a SEM graft in the skull base can be formed, a SEM graft in an endogenous sinus tissue can be formed, and/or an endonasal reservoir device can be introduced at least 3 days, 1 week, 2 weeks, 3 weeks, or 4 weeks prior to administering at least one pharmaceutical agent to the subject (e.g., administering the at least one pharmaceutical agent onto the SEM graft in the skull base, into the endonasal reservoir, or into the endonasal reservoir device).

In some embodiments, the subject can be a male, female, a child (e.g., between the age of 1 and 12), a teenager (e.g., between 13 and 19), an adult (e.g., at least 19 years old), at least 50 years old, at least 60 years old, at least 70 years old, or at least 80 years old. In some embodiments, the subject can be hospitalized or living in an assisted-living facility (e.g., a nursing home).

In some embodiments, the subject has been previously diagnosed as having a neurological disorder (e.g., a brain cancer or Parkinson's disease). Methods for the diagnosis of neurological disorders are described herein and additional methods for diagnosing neurological disorders are known in the art. In some embodiments, the subject may have been diagnosed as having a neurological disorder at least 5 years ago or 10 years ago, or may have received an alternative form of therapeutic treatment for at least 5 years or 10 years.

In some embodiments, the subject can be classified or identified as having a specific stage or severity of a neurological disorder. For example, subjects with Parkinson's disease (PD) can be classified as being in stage 1-5 of the disease. Stage one of PD is characterized by the observation of mild symptoms, such as tremors or shaking in one of the limbs, poor posture, loss of balance, and abnormal facial expressions. Stage two of PD is characterized by bilateral symptoms (affecting both limbs and both sides of the body) and difficulty walking, maintaining balance, and performing normal physical tasks. Stage three of PD is characterized by the inability to walk straight or to stand and a noticeable slowing of physical movements. Stage four of PD is characterized by rigidity, bradykinesia, and the inability to complete day-to-day tasks. Stage four PD subjects often cannot live independently. Stage five PD subjects have severe disability in their physical movements and usually require constant one-on-one medical or nursing care. A subject identified as being in any one of stages 1-5 of PD can be treated using the any of the methods described herein.

Alzheimer's disease (AD) patients can also be classified as having mild, moderate, or severe AD. Mild AD is characterized by memory loss for recent events, difficulty with problem solving, complex tasks, and sound judgments, changes in personality, difficulty organizing and expressing thoughts, and getting lost and misplacing belongings. Moderate AD is characterized by increasingly poor judgment, deepening confusion, even greater memory loss, the need for help with daily activities, and significant changes in personality and behavior. Severe AD is characterized by the loss of the ability to communicate coherently, the requirement of daily assistance with personal care, and decreased physical abilities (e.g., inability to sit or hold his or her head without support). A subject identified as having mild, moderate, or severe AD can be treated using the any of the methods described herein.

A subject with brain cancer can also be classified as being in stage 1-4 of the disease (stage 1 being low severity and stage 4 being the highest severity). In stage one of a brain cancer, the cancer cells have not invaded the surrounding tissue. In stage two of a brain cancer, the tumor size is larger and the cancer cells have most likely spread to the surrounding tissue. In stage three of a brain cancer, the cancer cells look different from normal cells, the surrounding tissue has become affected, and the tumor is classified as being more aggressive. In stage four of a brain cancer, the tumor has grown aggressively and the cancer can be difficult to treat. In some embodiments of any of the methods described herein, the subject can be identified as being in any one of stages 1-4 of a brain cancer and/or may have previously undergone surgery to remove all or part of a brain tumor.

In some embodiments, the subject has been identified as having an increased risk of developing a neurological disorder (e.g., expression of at least one biomarker or at least one gene sequence in a subject that is correlated with the development of a neurological disorder or a hereditary predisposition to developing a neurological disorder (e.g., familial history of the disease)). A subject can be diagnosed as having a neurological disorder or can be identified as having an increased risk of developing a neurological disorder by a health care professional (e.g., in a clinical laboratory, a clinic, a hospital, or an assisted-living facility (e.g., a nursing home or a hospice-care center)).

In some embodiments, the subject has been previously diagnosed as having pain (e.g., any of the forms of pain described herein). Methods for diagnosing or assessing pain in a subject are known in the art. For example, a number of methods for scoring pain are known in the art, including, but not limited to: Alder Hey Triage Pain Score, Brief Pain Inventory (BPI), Dallas Pain Questionnaire, Dolorimeter Pain Index (DPI), Faces Pain Scale, Face Legs Activity Cry Consolability Scale, McGill Pain Questionnaire (MPQ), Descriptor Differential Scale (DDS), Neck Pain and Disability Scale (NPAD), Numerical 11 Point Box (BS-11), Numeric Rating Scale (NRS-11), Roland-Morris Back Pain Questionnaire, Wong-Baker FACES Pain Rating Scale, and Visual Analog Scale (VAS). In some embodiments, the subject may have received an alternative form of pain treatment for at least 5 years or 10 years.

A subject can be treated in a hospital, a clinic (e.g., an out-patient clinic or primary care facility), or an assisted-living facility (e.g., a nursing home or hospice care center). The methods of treatment described herein can be performed by a health care professional (e.g., a nurse, a nursing assistant, a clinical technician, a physician's assistant, and a physician). The level of skill necessary to perform the treatment methods described herein will vary depending on the specific method performed. For example, administering at least one pharmaceutical agent to a subject by injection through the facial tissue can be performed by any health care professional, while the endoscopic administration or placement of at least one pharmaceutical agent or composition according to the methods described herein or the forming of the SEM graft in the skull base, the forming of the SEM in an endogenous sinus tissue surface, or the introduction of an endonasal reservoir device into an endogenous sinus tissue may require the skill of a physician or physician's assistant.

One or more doses of at least one of any of the pharmaceutical agents or compositions described herein can be administered to the subject. The at least one pharmaceutical agent or composition (e.g., any of the pharmaceutical agents or compositions described herein) can be administered in any dose or volume, at any frequency, or for any duration of time (e.g., any treatment period) described herein, in any combination. The at least one pharmaceutical agent or composition can be in any form (e.g., formulation) described herein. In some embodiments, the at least one pharmaceutical agent or composition is chronically administered to the subject (e.g., administered in two or more doses over a treatment period (e.g., over at least 1 week, 2 weeks, 1 months, 2 months, 3 months, 4 months, 5 months, 6 months, 1 year, 2 years, 3 years, 4 years, 5 years, 6 years, 7 years, 8 years, 9 years, 10 years, 15 years, 20 years, 25 years, or 30 years). Chronic administration can be performed until one or more specific therapeutic effects or outcomes is achieved (e.g., any of the therapeutic outcomes described herein) or can continue as long as the specific therapeutic effect or outcome continues to be observed in the subject (e.g., a decrease in the number or the severity, frequency, or duration of one or more symptoms of a neurological disorder, or a reduction of pain (e.g., reduction in at least one pain score) in the subject). A determination of the length and frequency of chronic administration can be made by a health care professional based on several factors described herein and known in the art.

As described herein, the two or more doses of the at least one pharmaceutical agent or composition can be administered at any frequency (e.g., a dose at least once a week, a dose at least once every two weeks, a dose at least one every three weeks, a dose at least once every month, a dose at least once every two months, or a dose once every three months). In some embodiments, only one dose of at least one chemotherapeutic agent or a composition containing at least one chemotherapeutic agent is administered to the subject. In some embodiments, only two, three, four, or five doses of at least one chemotherapeutic agent or a composition containing at least one chemotherapeutic agent is administered to the subject. In some embodiments, the one or more doses of at least one chemotherapeutic agent or a composition containing at least one chemotherapeutic agent is administered to the subject before or after a surgical procedure to resect or remove all or part of a brain tumor in the subject. Any form of a brain cancer may be treated using the methods described herein (e.g., a primary or a metastatic brain tumor).

In some embodiments of all of the methods described herein, the administering of the at least one pharmaceutical agent or composition described herein is performed by an endoscopic procedure (e.g., through the nasal canal of the subject). In some embodiments, the endoscopic procedure can include the use of a tube that allows the delivery of at least one pharmaceutical agent or composition (e.g., any of the pharmaceutical agents or compositions described herein) onto a SEM graft in a subject, into an endonasal reservoir, or into an endonasal reservoir device. In some embodiments, a pharmaceutical agent or composition is introduced into an endonasal reservoir device by injecting the agent/composition into the end of the tubing that is not connected to the device's body, where the end of the tubing not connected to the device's body is located in the sphenoid sinus. In these embodiments, the injection can be performed using an endoscopic procedure or through the use of a nasal speculum.

In some embodiments, the endoscopic instrument used to administer the at least one pharmaceutical agent or pharmaceutical composition further includes a light source or other means that allows for the visualization of the sinus or nasal tissues of the subject (e.g., visualization of the SEM graft in the skull base, the endonasal reservoir, and/or the endonasal reservoir device).

In some embodiments of the methods described herein, the endoscopic procedure can include the use of an instrument that allows the resection or manipulation of tissue (e.g., nasal mucosa, the mucoperiosteal layer, the bony layer, the intracranial dura, the arachnoid layer, a SEM, an endogenous sinus tissue proximal (e.g., roughly parallel) to an SEM graft in the subject) in the body or an incision in a tissue in the body (e.g., nasal mucosa, the mucoperiosteal layer, the intracranial dura, the arachnoid layer, a SEM, and an endogenous sinus tissue roughly parallel to an SEM graft in the subject). In some embodiments, the endoscopic procedure can include the use of forceps that can grab and hold tissue or a device (e.g., nasal mucosa, the mucoperiosteal layer, the bony layer, an excised SEM (e.g., an autologous SEM), a folded back or excised section of the intracranial dura and/or arachnoid layer, an endogenous sinus tissue proximal to an SEM graft in the subject, or an endonasal reservoir device), and can be used to place a SEM graft in the skull base of a subject, place a SEM graft into an endogenous sinus tissue surface, or place an endonasal reservoir device in the subject.

In some embodiments the administering of the at least one pharmaceutical agent or pharmaceutical composition described herein is performed by an interfacial procedure (e.g., by injection). In some embodiments of these methods, the endonasal tissue of the subject is imaged during the injection procedure, such that the tip of a cannula is positioned proximal (e.g., within 0.1 to 0.5 cm) to the SEM graft in the skull base, positioned in the endonasal reservoir (e.g., in the center of the endonasal reservoir), or positioned in the interior of the body of the endonasal reservoir device during the injection of the at least one pharmaceutical agent or composition. In some embodiments of these methods, the cannula preferably does not contact the SEM graft in the skull base. In some embodiments of all the methods described herein, the subject is sedated (e.g., mild sedation) or anesthetized (e.g., local facial or nasal anesthetization) prior and/or during the administration of the at least one pharmaceutical agent or pharmaceutical composition. In some embodiments, at least one sedative or anesthetic agent is administered to the subject prior to or during the administration of the at least one pharmaceutical agent or pharmaceutical composition. The at least one sedative or anesthetic agent may be formulated using any methods known in the art (e.g., a gas, a liquid for injection (e.g., intramuscular, intravenous, intraarterial, or intracranial injection)).

In some embodiments of all the methods described herein, the subject may be administered two or more doses (e.g., chronic administration) of at least one of any of the pharmaceutical agents or compositions described herein. As described herein, the at least one pharmaceutical composition or agent administered can decompose in the body into degradation products (e.g., insoluble or partially insoluble degradation products) that are not naturally cleared by mucociliary clearance from the endonasal passages of the subject. Therefore, some embodiments of the methods described herein further include lavaging the endonasal tissue (e.g., lavaging the endonasal reservoir in the subject) or the endonasal reservoir device placed in the subject prior to the administration of an additional or second dose of a pharmaceutical composition. As is known in the art, lavage of a body cavity or tissue may be performed using any biocompatible and/or homeostatic solution (a lavage fluid, e.g., saline). In some embodiments, a lavage of the endonasal cavity in a subject may be performed endoscopically by inserting an instrument through the nasal canal of a subject into the endonasal cavity of the subject. This instrument can be equipped with tubing which allows the introduction of a biocompatible and/or homeostatic solution into the endonasal cavity or the endonasal reservoir. In some embodiments, the lavage of the endonasal reservoir device can be performed by injecting and subsequently removing a biocompatible and/or homeostatic solution into and out of the body of the device. For example, the lavage of the device can be performed by injecting and subsequently removing the biocompatible and/or homeostatic lavage solution through the tubing of the device (e.g., through the end of the tubing that is not connected to the device's body, e.g., located in the sphenoid sinus).

The instrument used to perform the lavage can also be equipped with an empty tube connected to a vacuum apparatus to allow removal of the biocompatible and/or homeostatic solution containing one of more of the degradation products. As is known in the art, the volume of the lavage fluid utilized in these methods may vary and can readily be determined by a health care professional during the procedure. A lavage may be performed prior to the administration of each dosage of the at least one pharmaceutical agent or composition, or a lavage can be performed prior to every other administration of a dosage of the at least one pharmaceutical agent or composition. In some embodiments, a lavage can be performed at any individual administration in a chronic treatment regime upon a determination by a health care profession that an accumulation of degradation products is present in a subject's nasal or sinus tissue, endonasal reservoir, or endonasal reservoir device (e.g., upon observation or detection of one of more symptoms of nasal/sinus blockage or occlusion (e.g., by endoscopy, computed tomography, and magnetic resonance imaging), upon observation or detection of one of more symptoms of sinitis, or upon observation or detection of one of more symptoms of inflammation or infection in the nasal/sinus cavity or an endonasal reservoir in the subject).

As described herein, the methods of treatment described herein can result in a decrease (e.g., a significant, observable, or detectable decrease) in the number or the severity, frequency, or duration of at least one symptom of a neurological disorder in a subject. As is known in the art, the symptoms of individual neurological disorders can differ. A number of common symptoms of individual neurological disorders are described herein. These symptoms of neurological disorders (as well as any other symptoms known in the art) can be detected and observed by health care professionals. The efficacy of treatment provided by any of the methods described herein can be determined by a health care professional by observing or detecting a decrease in the number or the severity, frequency, or duration of at least one symptom of a neurological disorder in a subject receiving treatment (e.g., as compared to the number or the severity, frequency, or duration of symptoms in the same subject prior to treatment or the number or the severity, frequency, or duration of symptoms in another subject having the same neurological disorder but not receiving treatment). In some embodiments, the administering results in an increase (e.g., an observable or detectable increase) in cognitive function or memory in a subject (e.g., a subject having Alzheimer's disease). In some embodiments, the administering results in a decrease (e.g., an observable or detectable decrease) in the rate of loss of neurons and/or synapses in the cerebral cortex or subcortical regions in the brain of a subject having Alzheimer's disease or in an animal model of Alzheimer's disease (e.g., as compared to the rate of loss of neurons and/or synapses in the cerebral cortex or subcortical regions of a subject having Alzheimer's disease or an animal model of Alzheimer's disease not receiving treatment or receiving a different therapeutic treatment). In some embodiments, the administering results in a decrease (e.g., an observable or detectable decrease) in the amount of amyloid plaques and/or neurofibrillary tangles or the rate of formation of amyloid plaques and/or neurofibrillary tangles in the cerebral cortex or subcortical regions in the brain of a subject having Alzheimer's disease or in an animal model of Alzheimer's disease (e.g., as compared to the amount of amyloid plaques and/or neurofibrillary tangles or the rate of formation of amyloid plaques and/or neurofibrillary tangles in the cerebral cortex or subcortical regions in the brain of a subject having Alzheimer's disease or an animal model of Alzheimer's disease not receiving treatment or receiving a different therapeutic treatment).

In some embodiments, the administering results in a decrease (e.g., a detectable or observable decrease) in one or more symptoms of Parkinson's disease in a subject, e.g., decreased tremor, bradykinesia, and/or rigidity (e.g., as compared to the same subject prior to treatment or another subject having Parkinson's disease but not receiving treatment). In some embodiments, the administering results in one or more of the following effects: a decrease (e.g., a significant, observable, or detectable decrease) in unregulated or mis-regulated cell growth (e.g., cancer cell growth), an increase (e.g., a significant, observable, or detectable increase) in cancer cell death (e.g., necrosis or apoptosis), a decrease in neuron cell death (e.g., apoptosis or necrosis), a decrease in the loss of axons and/or dendrites or the rate of the loss of axons and/or dendrites, a decrease in protein misfolding and/or aggregation (e.g., β-amyloid mis-folding or aggregation), an increase or decrease in neurohormone or neurotransmitter production or turn-over, an increase or decrease in neurohormone or neurotransmitter receptor activity, an increase or decrease in synaptic transmission between neurons, and an increase or decrease in neuronal intracellular signaling pathways.

As described herein, the methods of treating pain described herein can result in a decrease (e.g., a significant, observable, or detectable decrease) in the severity, frequency, or duration of pain in a subject. As is known in the art, there are a variety of different causes and types of pain. Different pain scoring scales have been developed in order to allow health care professionals to quantitate pain in subjects. The efficacy of pain treatment provided by the methods described herein can be determined by a health care professional by observing or detecting a decrease in the severity, frequency, or duration of pain (e.g., pain score) in a subject receiving treatment (e.g., as compared to the severity, frequency, or duration of pain (e.g., pain score) in the same subject prior to treatment or the severity, frequency, or duration of pain in another subject having the etiology (e.g., caused by the same disease or disorder) but not receiving treatment).

In some embodiments of any of the methods described herein, the subject can be administered one or more additional therapeutic agents. Non-limiting examples of one or more additional therapeutic agents that can be administered include sedatives and analgesics. Non-limiting examples of sedatives include: barbituates (e.g., amobarbital, pentobarbital, secobarbital, and phenobarbital), benzodiazepines (e.g., clonazepam, diazepam, estazolam, flunitrazepam, lorazepam, midazolam, nitrazepam, oxazepam, traizolam, temazepam, chlordiazepoxide, alprazolam), and anti-histamines (e.g., diphenhydramine, dimenhydrinate, doxylamine, and promethazine). Non-limiting examples of analgesics include: opiates (e.g., morphine, codeine, thebaine, and papverine), non-steroidal anti-inflammatory drugs (e.g., acetylsalicylic acid, diflusinal, salsalate, ibuprofen, naproxen, fenoprofen, ketoprofen, flurbiprofen, oxaprozin, loxoprofen, indomethacin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, licofelone, and tolfenamic acid), and COX-2 inhibitors celecoxib, etoricoxib, and firocoxib).

The methods described herein provide for the treatment of a neurological disease or pain by the targeted delivery of at least one pharmaceutical agent (e.g., analgesic) or composition (e.g., composition containing an alagesic) to the CNS of a subject. In some embodiments, the methods decrease (e.g., an observable or detectable decrease) or avoid the toxicity or adverse effects that are observed when the same pharmaceutical agent(s) or composition(s) is administered systemically (e.g., to a majority of the tissues in the subject). In some embodiments, the methods provided herein allow for an increased dosage of at least one pharmaceutical agent to be administered to the subject (e.g., a dosage that is greater than the maximum sub-toxic dosage that can be administered systemically to a subject). In some embodiments, the methods eliminate the variability in dosage levels of at least one pharmaceutical agent in the subject (e.g., as a result of subject non-compliance with administration schedules). In some embodiments, the methods reduce the number of spikes in the level of at least one pharmaceutical agent in the CNS of a subject compared to the number of spikes in the level of at least one pharmaceutical agent in the CNS when the at least one pharmaceutical agent is administered orally or by intramuscular, intravenous, intraarterial, or intracranial injection.

EXAMPLES

The invention is further described in the following examples, which do not limit the scope of the invention described in the claims.

Example 1

Exemplary Surgical Procedure in a Human

An endoscopic procedure was performed on a subject having a brain tumor. In this procedure, the tumor and a section of bone and the meninges were removed from the skull base of the subject (FIG. 10A). A SEM graft was placed over the opening generated following the removal of the tumor, bone, and the meninges from the skull base (FIG. 10B). The SEM graft placed over the opening in the bone and meninges in the skull base healed to prevent leakage of the CSF from the subarachnoid space (FIG. 10C).

Example 2

Transport of Molecules Across an SEM Graft in a Mouse Model

Experiments were performed in mice to demonstrate that the administration of agents onto an SEM graft over the skull of a mouse results in delivery of the agents to the central nervous system of the mouse.

Figure 13:
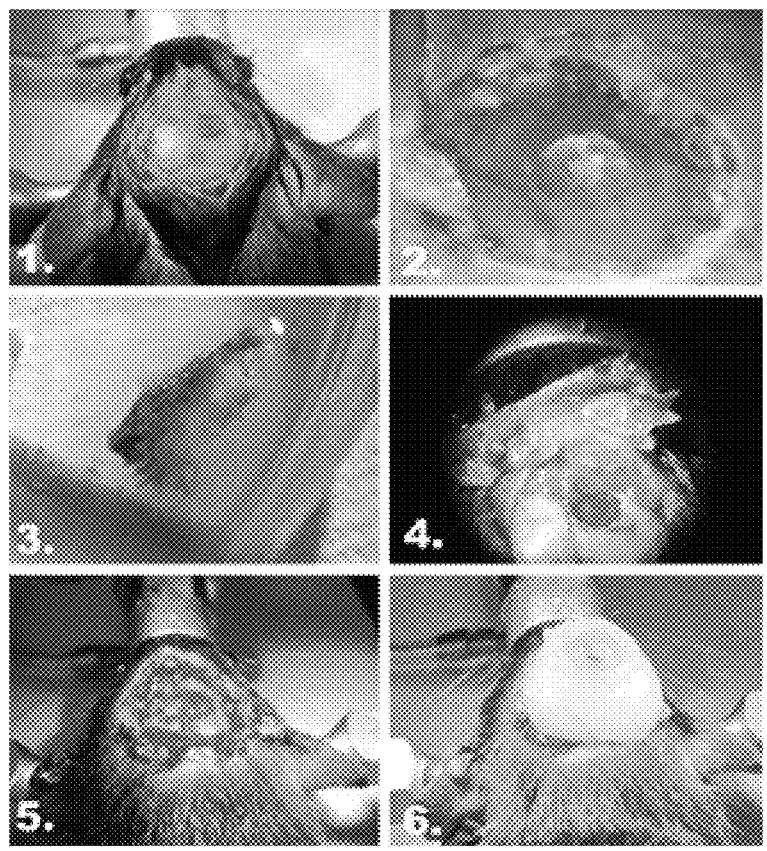
FIG. 13 is a set of six photographs showing an exemplary heterotopic mucosal grafting technique in a murine model.
Figures 14A, 14B:
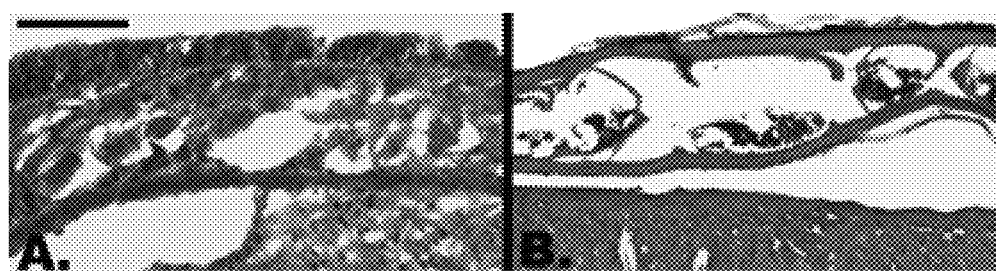
FIGS. 14A-B are a pair of photomicrographs. 14A shows a hematoxylin and eosin (H&E) stained section of mucosal graft implant in direct continuity with underlying brain parenchyma. Note the intact epithelial layer consisting of pseudostratified columnar epithelium (bar=200 um. 14B shows an intact parietal bone for comparison with typical appearance of the inner and outer cortical tables with their associated diploic space.
Figure 15:
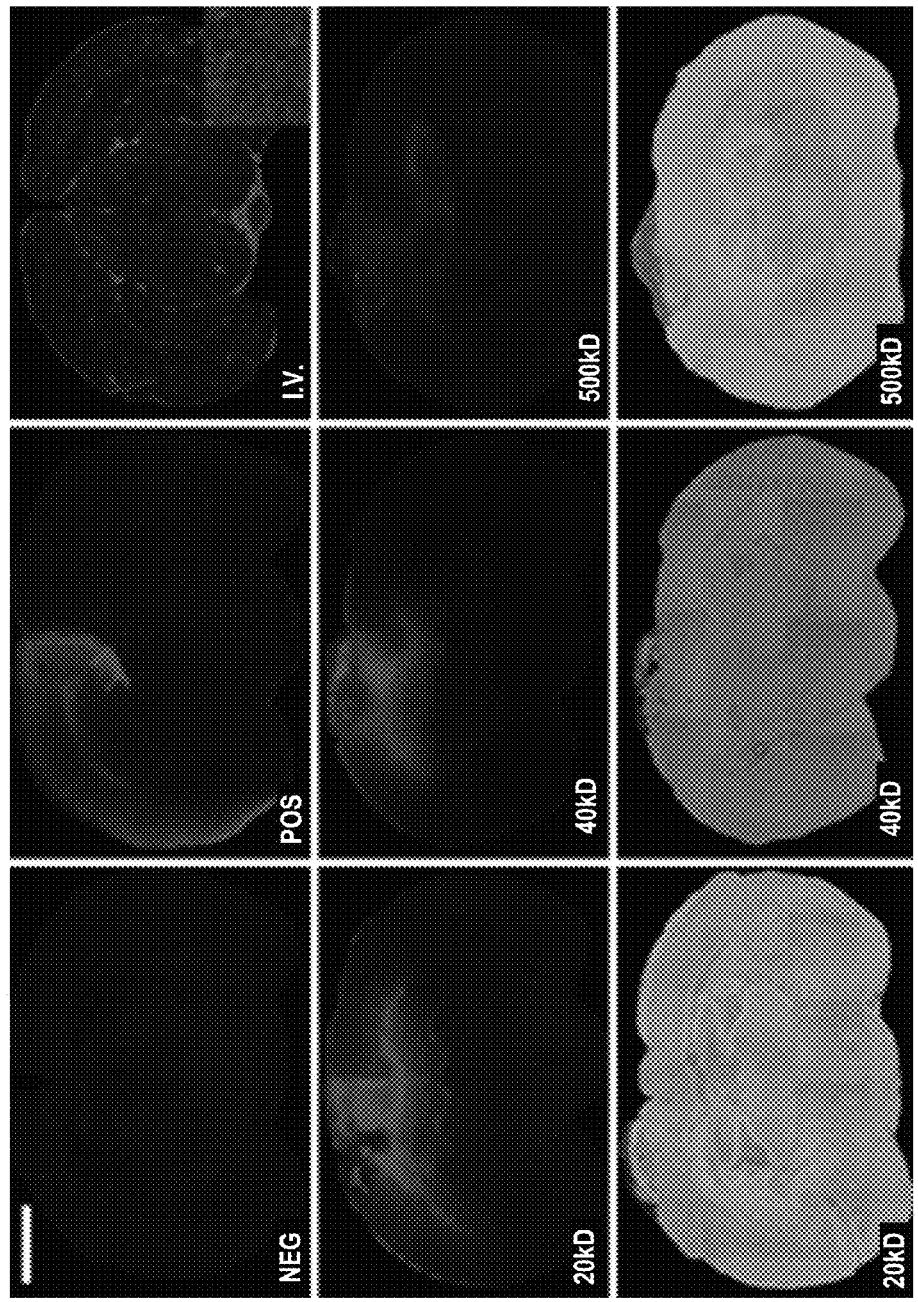
FIG. 15 is a set of nine fluorescent microscopic images demonstrating transmucosal rhodamine-dextran delivery (bar=1 mm, bregma −1.06 mm). Negative (NEG) and positive (POS) control images represent delivery through intact dura or direct parenchymal delivery with no intervening dura or mucosa. Note the filling of the intracranial vasculature following intravenous (I.V.) delivery with no transvascular diffusion consistent with an intact blood-brain barrier (evident in high magnification inset at 40×). A molecular weight-dependent successive reduction in area and intensity of transmucosal delivery is seen between 20, 40, and 500 kDa rhodamine-dextran. Bottom row represents matched brightfield images demonstrating the mucosal graft stained with the Evans Blue (M.W. 961 Da) used to confirm mucosal graft integrity prior to dosing.
Figure 16:
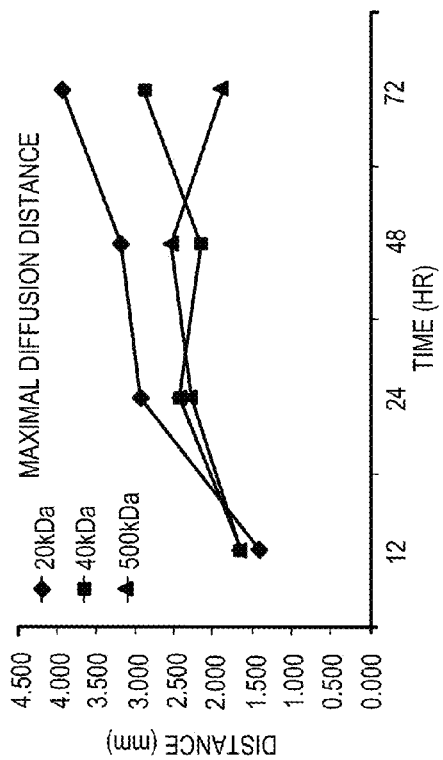
FIG. 16 is a bar graph showing whole brain luminosity (bregma −1.06 mm) directly below the mucosal graft (n=2, *,**=p<0.05). All markers demonstrated successful diffusion through the mucosal graft after 24 h. As molecular weight increases, there is a trend towards decreased marker diffusion as calculated by whole brain luminosity (NS). As expected there was negligible diffusion through the intact dura and arachnoid due to the preservation of the blood-CSF barrier (negative control). There was a significant increase in delivery in the positive control in which marker was exposed directly to the brain after removal of the dura and arachnoid.
Figure 18:
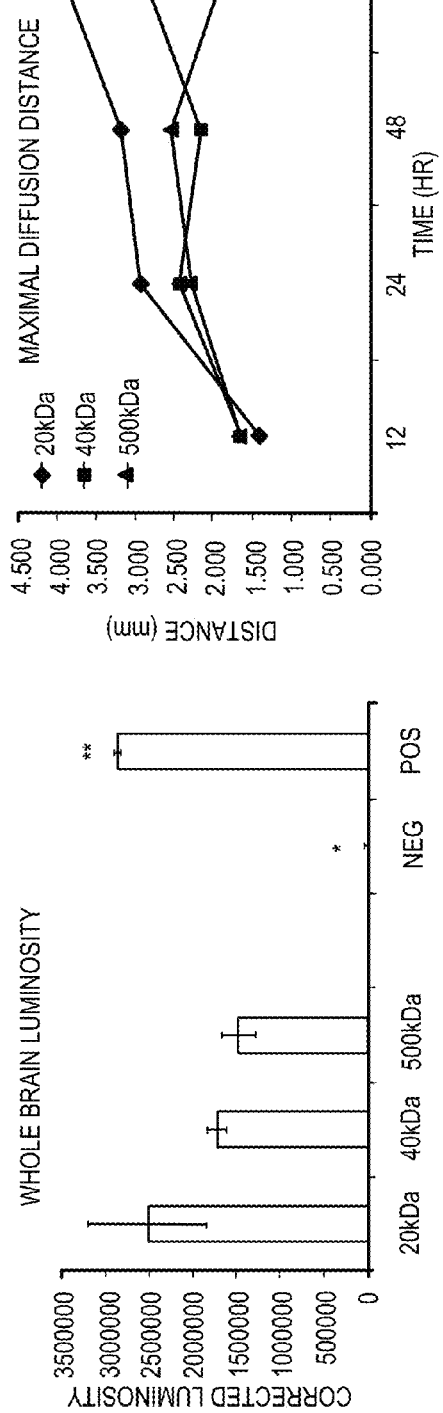
FIG. 18 is a bar graph showing the maximal length of coronal diffusion from mucosal graft into the brain by time and molecular weight. Note that the diffusion path length was dependent both on the duration of exposure and molecular weight of the marker (n=2). The maximal diffusion distance at 72 hrs was significantly greater for the 20 kDa marker than the 40 or 500 kDa markers (p<0.05).
Figure 17:
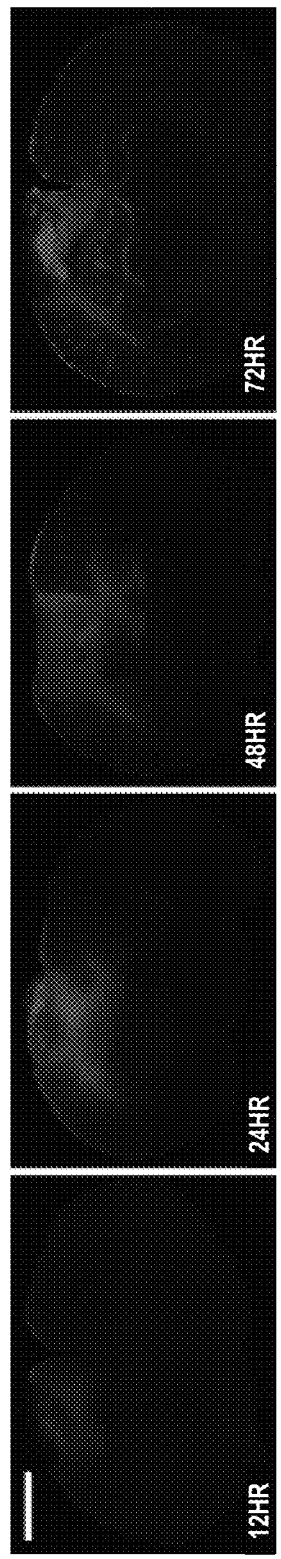
FIG. 17 is a set of four fluorescent microscopic images demonstrating an increase in area and intensity of transmucosal rhodamine-dextran delivery over time (bar=1 mm, bregma −1.06 mm, 40 kDa rhodamine-dextran).

Heterotopic mucosal grafting surgery was performed in adult mice prior to the administration of a test agent to the mice, as shown in FIG. 13. As shown in panel 1, a dural sparing 3 mm parasagittal craniotomy was performed over the right parietal bone posterior to the sagittal suture. As shown in panel 2, the dura and arachnoid were reflected using a small aliquot of vet bond. In panel 3, the septum was harvested from a donor mouse en bloc. Panel 4, the mucosa of the donor mouse was implanted over the craniotomy site (e.g., an SEM graft) and the skin was closed.

Histologic analysis showed that engrafting was complete after 1 week of healing providing an acceptable time frame to initiate marker exposure (FIG. 12).

In Panel 5, after one week the mucosal graft was exposed following reflection of the skin flaps. In Panel 6, a 100 uL reservoir (a plastic cuff) was implanted over the mucosal graft and affixed to the skull with dental cement. The reservoir was then used to dose the graft with the desired solution, see FIG. 11. Graft integrity was verified using Evans blue dye, a common stain for epithelial barrier integrity; the ability of the graft to inhibit parenchymal staining was a reliable marker for graft integrity and complete graft healing. All specimens were examined under brightfield microscopy to ensure graft integrity prior to fluorescent analysis.

One hundred microliters of Fluorescein sodium (FI Na) or FITC-dextran (500 μg/ml) having an average molecular weight of 10, 20, 40, or 70 kDa were applied to the SEM graft formed over the skull. Individual mice were sacrificed at 30, 60, 120, or 240 minutes or 12-72 hours after dosing. Tissue sections were fixed using a perfusion cocktail of 4% paraformaldehyde, 1% Evans Blue (EB), and 0.01% Hoechst as described by del Valle et al. (J. Neurosci. Methods 174:42-49, 2008).

The graft was centered around bregma −1.5 mm and diffusion was determined at 3 coronal sections to capture striatal diffusion (bregma 1.18 mm), immediate submucosal diffusion (bregma −1.06 mm), and substantia nigra diffusion (bregma −2.80 mm). Delivery was calculated by creating a weighted average of the intensity of fluorescent staining over the total area of marker diffusion (luminosity score). The maximal diffusion distance from the center of the graft was also calculated using standard image processing software.

Figure 19:
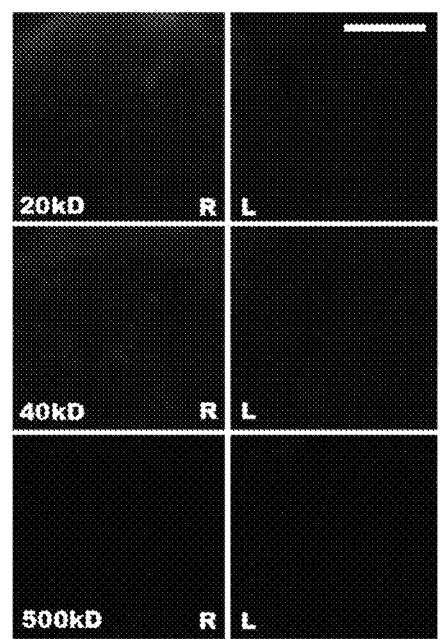
FIG. 19 is a set of six fluorescent microscopic images demonstrating transmucosal rhodamine-dextran delivery to the striatum (bregma 1.18 mm, bar=0.5 mm). Diffusion into the right striatum (ipsilateral to mucosal graft) occurs in a molecular weight dependent fashion while contralateral diffusion to the left striatum is negligible.
Figure 20:
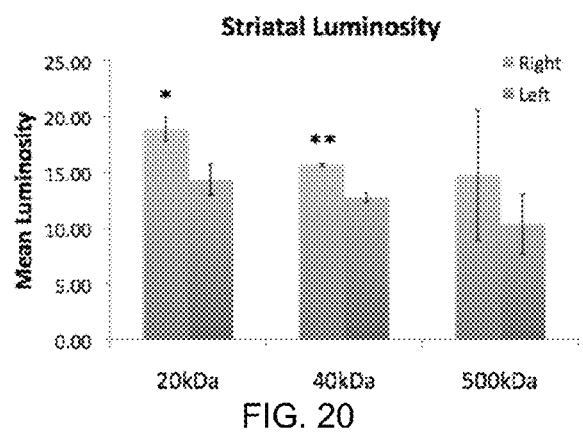
FIG. 20 is a bar graph showing mean luminosity of the right and left striatum demonstrating increased marker diffusion into the right striatum (ipsilateral to the mucosal graft) as molecular weight decreases (n=2). Delivery to the right striatum was significantly greater than left for the 20 and 40 kDa markers (*,**, p<0.05).

The findings demonstrated that, although diffusion was limited over the shorter time course, at 12-72 hours the mucosal graft technique was capable of reproducible high molecular weight marker delivery up to 500 kDa directly into the CNS. The luminosity score and maximal diffusion distance followed a predictable pattern with improved delivery as molecular weight decreased and exposure time increased (FIGS. 15-18). The data demonstrates successful marker delivery to the striatum ipsilateral to the mucosal graft (right side) for the 20 and 40 kDa rhodamine-dextran markers. Delivery to the ipsilateral striatum with the 500 kDa marker and contralateral striatum with all markers was negligible (FIGS. 19 and 20). Delivery to the substantia nigra was negligible for all markers.

Example 3

Phenotypic Effect of Agent Delivery to the Central Nervous System Using an SEM Graft Additional experiments were performed to determine whether administration of an agent directly onto a SEM graft over the skull resulted in a phenotypic effect in a mouse model. These experiments were based on the observation of a particular behavioral pattern in a Parkinson's Disease mouse model following the administration of apomorphine. Successful administration of apomorphine to the central nervous system in this mouse model (via direct administration onto a SEM graft formed over the skull) was manifested by rotational behavior in the mice. The details of these experiments are described below.

Experimental Design

The mice underwent unilateral striatal 6-hydroxydopamine (6-OHDA) injection (3.2 μg/μL, 0.5 μL/min×4 min) according to Francardo et al. (*Neurobiol. Dis.* 42:327-340, 2011). Two-week post-injury mice underwent testing with apomorphine (300 μL, 0.065 mg/mL, $t^{1/2}$30-40 min) via single bolus IP injection or continuous administration onto a SEM graft over the skull via a drug-eluting hydrogel. The placement of a SEM graft over the skull of the mice was performed as described above. The duration of rotational behavior was determined in the treated mice.

Quantification of Rotation

The position of the mice was recorded by a camera (while they move freely in an arena). The number of contralateral rotations per minute was quantified using a custom analysis program written in Matlab and C++. Statistical analyses were performed using a Student's t-test to compare results between treatment groups (Stata v6.0).

Results

Figure 21:
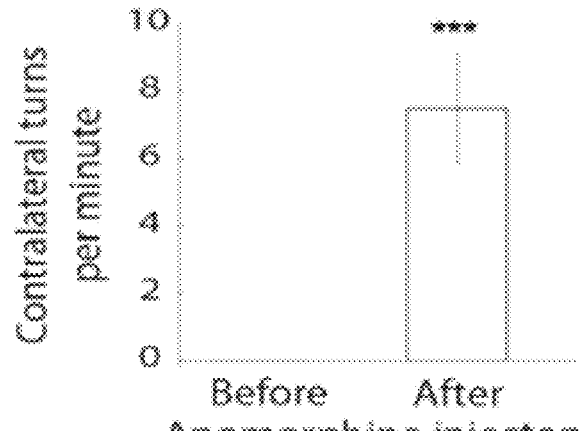
FIG. 21 is a graph showing the number of contralateral turns observed per minute in a 6-hydroxydopamine (6-OHDA) injury Parkinson's Disease mouse model before or after intraperitoneal injection with apomorphine.

Mice intraperitoneally administered apomorphine as described above were shown to have increased rotational behavior (FIG. 21). Based on these data and the above described data, a more rapid onset and prolongation of rotational behavior is expected for mice administered apomorphine across an SEM graft over the skull compared to mice administered apomorphine by intraperitoneal injection.

Example 4

Neuroprotective Effect of Agents Delivered Across a SEM Graft

Additional experiments will be performed to determine whether delivery of agents to the central nervous system through a SEM graft over the skull will result in a neuroprotective effect in mice. These experiments will be performed as described below.

Experimental Design

Aged (8-month old) mice will be assigned to groups listed in Table 1. Treatment with 6-OHDA will be performed as described above. The formation of a SEM graft over the skull of these mice will be performed as described above.

TABLE 1

|  | TransSMM GCNF (5 nmol × 10 d) | IP GDNF (5 nmol × 10 d) |
|---|---|---|
| Intrastriatal 6-OHDA | N = 4 | N = 4 |
| Instrastriatal SHAM | N = 4 | N = 4 |

Tyrosine-Hydroxylase (TH) Immunostaining

The brains of these mice will be fixed and processed for TH immunostaining as described by Dietz et al. (*Brain Res.* 1082:61-66, 2006). Briefly, brains will be sectioned followed by incubation with primary (anti-TH, 1:1000) and secondary antibodies (anti-rabbit Cy3-conjugated IgG, 1:200).

Quantification of TH Immunoreactivity

Coronal sections of the rostrocaudal SN axis will be analyzed (Bregma −2.46 to −4.08). The total number of Substantia Nigra Pars Compacta-stained neurons will be counted using a superimposed grid. CSF and plasma glial cell line-derived neurotrophic factor (GDNF) levels will be determined by enzyme-linked immunosorbent assays (ELISAs). Data analysis will use a one-way analysis of variance (ANOVA) and Fisher's protected least squares difference (PLSD) test (95% significance) for multiple comparisons.

Predicted Results

Based on prior injury models, an increased preservation of TH staining in mice administered GDNF across the SEM graft over the skull compared to mice administered GDNF intraperitoneally is expected in this mouse model.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of delivering at least one pharmaceutical agent to the central nervous system of a subject diagnosed with a brain cancer, the method comprising directly administering at least one pharmaceutical agent onto a semipermeable epithelial membrane (SEM) graft in the skull base of the subject.

2. The method of claim 1, wherein the at least one pharmaceutical agent is administered into an endonasal reservoir.

3. The method of claim 1, wherein the at least one pharmaceutical agent is placed into an endonasal reservoir device in an endogenous sinus tissue of the subject, wherein the device comprises at least one opening or permeable surface proximal to the SEM graft in the skull base and the at least one pharmaceutical agent in the endonasal reservoir device is administered onto the SEM graft in the skull base.

4. The method of claim 1, further comprising forming a semipermeable epithelial membrane (SEM) graft in the skull base of the subject.

5. The method of claim 4, further comprising forming a SEM graft over an endogenous sinus tissue or in a position proximal to the SEM graft in the skull base, where the SEM graft over the endogenous sinus tissue or in the position proximal to the SEM graft in the skull base forms an endonasal reservoir.

6. The method of claim 4, further comprising:
introducing an endonasal reservoir device comprising at least one opening or permeable surface into an endogenous sinus tissue of the subject; and
placing the at least one pharmaceutical agent into the endonasal reservoir device; wherein the at least one opening or permeable surface is proximal to the SEM graft in the skull base and the at least one pharmaceutical agent in the endonasal reservoir device is administered onto the SEM graft in the skull base.

7. The method of claim 1, wherein the forming, introducing, placing, or administering is performed by an endoscopic or interfacial procedure.

8. The method of claim 1, wherein the SEM graft in the skull base is formed from sinonasal mucosa.

9. The method of claim 1, wherein the SEM graft in the skull base is formed in the posterior frontal table, cribiform plate/ethmoid roof, planum sphenoidale, tuberculum, sella, clival recess, clivus, or cervical spine.

10. The method of claim 1, wherein the at least one pharmaceutical agent is formulated as a component of a biodegradable biocompatible polymer.

11. The method of claim 10, wherein the biodegradable biocompatible polymer is cationic.

12. The method of claim 10, wherein the biodegradable biocompatible polymer is a gel.

13. The method of claim 12, wherein the gel is an alginate gel, a cellulose-based gel, or a chitosan-based gel.

14. The method of claim 13, wherein the alginate gel is sodium alginate.

15. The method of claim 13, wherein the cellulose-based gel is carboxymethyl cellulose or carboxyethyl cellulose.

16. The method of claim 13, wherein the chitosan-based gel is chitosan glycerophosphate.

17. The method of claim 1, wherein the at least one pharmaceutical agent is formulated as a liquid.

18. The method of claim 17, wherein the liquid is a thermosetting liquid.

19. The method of any claim 1, wherein the at least one pharmaceutical agent is administered in a sustained-release formulation.

20. The method of claim 1, wherein the at least one pharmaceutical agent has a molecular size of greater than 500 Daltons, has a net negative or positive charge, or is a polar molecule.

21. The method of claim 1, wherein the at least one pharmaceutical agent comprises a chemotherapeutic agent.

22. The method claim 21, wherein the chemotherapeutic agent is selected from the group consisting of: cyclophosphamide, mechlorethamine, chlorabucil, melphalan, daunorubicin, doxorubicin, epirubicin, idarubicin, mitoxantrone, valrubicin, paclitaxel, docetaxel, etoposide, teniposide, tafluposide, azacitidine, axathioprine, capecitabine, cytarabine, doxifluridine, fluorouracil, gemcitabine, mercaptopurine, methotrexate, tioguanine, bleomycin, carboplatin, cisplatin, oxaliplatin, all-trans retinoic acid, vinblastine, vincristine, vindesine, vinorelbine, and bevacizumab.

23. The method of claim 1, wherein the brain cancer is selected from the group consisting of: glioblastoma multiforme, oligodendroglioma, astrocytoma, oligogastrocytoma, ependymoma, medulloblastoma, and meningioma.

* * * * *

UNITED STATES PATENT AND TRADEMARK OFFICE
CERTIFICATE OF CORRECTION

| | | |
|---|---|---|
| PATENT NO. | : 9,439,852 B2 | Page 1 of 1 |
| APPLICATION NO. | : 14/739872 | |
| DATED | : September 13, 2016 | |
| INVENTOR(S) | : Benjamin S. Bleier | |

It is certified that error appears in the above-identified patent and that said Letters Patent is hereby corrected as shown below:

On the Title Page

Item (56), Column 2 (Publications), Line 7, delete "glycerophasphate-based" and insert -- glycerophosphate-based --;

In the Claims

In Column 42, Line 2, in Claim 9, delete "cribiform" and insert -- cribriform --;

In Column 42, Line 23, in Claim 19, delete "method of any claim" and insert -- method of claim --;

In Column 42, Line 32, in Claim 22, delete "method claim" and insert -- method of claim --;

In Column 42, Line 34, in Claim 22, delete "chlorabucil," and insert -- chlorambucil, --;

In Column 42, Line 37, in Claim 22, delete "axathioprine," and insert -- azathioprine, --; and In Column 42, Line 44, in Claim 23, delete "oligogastrocytoma," and insert -- oligoastrocytoma, --.

Signed and Sealed this
Twenty-seventh Day of December, 2016

Michelle K. Lee
*Director of the United States Patent and Trademark Office*